(12) United States Patent
McArthur

(10) Patent No.: US 9,024,005 B2
(45) Date of Patent: May 5, 2015

(54) NUCLEIC ACID COMPLEXES

(75) Inventor: Michael McArthur, Norwich (GB)

(73) Assignee: Procarta Biosystems Ltd, Norwich (GB)

(*) Notice: Subject to any disclaimer, the term of this patent is extended or adjusted under 35 U.S.C. 154(b) by 0 days.

(21) Appl. No.: 13/578,625

(22) PCT Filed: Feb. 11, 2011

(86) PCT No.: PCT/GB2011/050263
§ 371 (c)(1),
(2), (4) Date: Aug. 12, 2012

(87) PCT Pub. No.: WO2011/098829
PCT Pub. Date: Aug. 18, 2011

(65) Prior Publication Data
US 2013/0059775 A1   Mar. 7, 2013

Related U.S. Application Data

(60) Provisional application No. 61/304,087, filed on Feb. 12, 2010.

(30) Foreign Application Priority Data

Feb. 12, 2010   (GB) .................................. 1002413.1

(51) Int. Cl.
| | |
|---|---|
| C07H 21/04 | (2006.01) |
| A61K 47/48 | (2006.01) |
| A61K 38/12 | (2006.01) |
| A61K 38/17 | (2006.01) |
| C12N 15/113 | (2010.01) |

(52) U.S. Cl.
CPC ........... *A61K 47/48238* (2013.01); *A61K 38/12* (2013.01); *A61K 38/1703* (2013.01); *A61K 47/48115* (2013.01); *A61K 47/48246* (2013.01); *A61K 47/48792* (2013.01); *C12N 15/113* (2013.01); *C12N 2310/13* (2013.01); *C12N 2310/351* (2013.01); *C12N 2320/32* (2013.01); *A61K 47/4803* (2013.01)

(58) Field of Classification Search
None
See application file for complete search history.

(56) References Cited

U.S. PATENT DOCUMENTS

| | | | |
|---|---|---|---|
| 5,977,084 A | 11/1999 | Szoka, Jr. et al. | |
| 6,133,026 A | 10/2000 | Huang et al. | |
| 6,551,795 B1 | 4/2003 | Rubenfield et al. | |
| 2007/0011759 A1* | 1/2007 | Khan | 800/278 |
| 2007/0014840 A1 | 1/2007 | Lee et al. | |
| 2007/0104775 A1* | 5/2007 | Panzner et al. | 424/450 |
| 2009/0099108 A1 | 4/2009 | Jones | |
| 2014/0274800 A1 | 9/2014 | McArthur | |

FOREIGN PATENT DOCUMENTS

| | | | |
|---|---|---|---|
| EP | 2266626 | 12/2010 | |
| WO | WO 93/19768 | 10/1993 | |
| WO | WO 94/23699 | 10/1994 | |
| WO | WO 95/34647 | 12/1995 | |
| WO | WO9730070 A1 * | 8/1997 | ............. C07K 14/31 |
| WO | WO 99/13096 A1 | 3/1999 | |
| WO | WO9913096 A1 * | 3/1999 | ............. C12N 15/87 |
| WO | WO 01/75067 A2 | 10/2001 | |
| WO | WO 2004/016754 | 2/2004 | |
| WO | WO 2004030699 A1 * | 4/2004 | ............. C07K 14/31 |
| WO | WO 2004/067709 A2 | 8/2004 | |
| WO | WO 2005/062854 | 7/2005 | |
| WO | WO 2007/013480 | 2/2007 | |
| WO | WO 2007/137301 | 11/2007 | |
| WO | WO 2008/024389 | 2/2008 | |
| WO | WO 2008/092142 | 7/2008 | |
| WO | WO 2009/044154 A2 | 4/2009 | |
| WO | WO 2010/038083 | 4/2010 | |
| WO | WO 2011/098829 A1 | 8/2011 | |
| WO | WO 2011/121357 | 10/2011 | |

OTHER PUBLICATIONS

Oren and Shai, Mode of Linear Amphipathic α-Helical Antimicrobial Peptides, Biopolymers (Peptide Science) vol. 47, 451-463 (1998).*
Buck et al., The Bacterial Enhancer-Dependent ζ54(θN) Transcription Factor, J. Bacteriol. Aug. 2000 vol. 182 No. 15 4129-4136.*
Galanakis, J. Med. Chem. 1995, 38, 3536-3546.*
Weissig et al.(2006) J. Liposome Research 16:249-264.*
Mann and Dzau, Therapeutic applications of transcription factor decoy oligonucleotides, The Journal of Clinical Investigation, Nov. 2000, vol. 106, No. 9, pp. 1071-1075.*
Coles et al., Trial of Dequalinium for Skin Infections, British Medical Jl., Oct. 25, 1998, pp. 1014-1017.*
Lim et al., Sequence-independent inhibition of RNA transcription by DNA dumbbells and other decoys, Nucleic Acids Res., 1997, vol. 25, No. 3, pp. 575-581.*
Gutierrez-Lugo et al., Dequalinium, a New Inhibitor of Mycobacterium tuberculosis Mycothiol Ligase Identified by High-Throughput Screening, Jl. of Molecular Screening, 2009 14:643 (original online publication date Jun. 12, 2009).*

(Continued)

*Primary Examiner* — Karlheinz R Skowronek
*Assistant Examiner* — Joseph Fischer
(74) *Attorney, Agent, or Firm* — Knobbe, Martens, Olson & Bear LLP

(57) ABSTRACT

The present invention relates to complexes of transcription factor decoys, their delivery to bacteria and their formulation. In particular, the present invention resides in an antibacterial complex comprising a nucleic acid sequence and one or more delivery moieties selected from quaternary amine compounds; bis-aminoalkanes and unsaturated derivatives thereof, wherein the amino component of the aminoalkane is an amino group forming part of a heterocyclic ring; and an antibacterial peptide.

3 Claims, 21 Drawing Sheets

(56) References Cited

OTHER PUBLICATIONS

Figure 1:
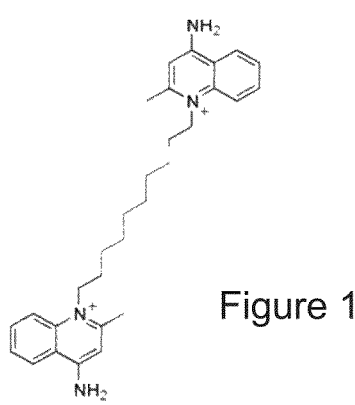

Viera et al., Restoration of Vancomycin Susceptibility in *Enterococcus faecilis* by Antiresistance Determinant Gene Transfer, Antimicrobial Agents and Chemotherapy, Mar. 2001, p. 973-975.*
Weissig et al., DNA binding cationic bolasomes with delocalized charge center a structure-activity relationship study, S.T.P. Pharma Sciences, 11(1)91-96 2001.*
Boyd et al., VanG-Type Vancomycin-Resistant *Enterococcus faecilis* Strains Isolated in Canada, Antimicrobial Agents and Chemotherapy, Jun. 2006, p. 2217-2221.*
Gross et al., Bacterial Sigma Factors, Chapter 6, pp. 129-176, Cold Spring Harbor, 1992.*
Weissig et al., "DNA binding cationic blomasones etc . . . " STP Pharma sciences 2991 FR, vol. 11, No. 1, 2001, pp. 91-96, p. 92 col. 1 para 3 figs 1 and 2, table 2.
Legendre et al, "Biochemical, Morphological and Functional etc.", J. Liposome Res. vol. 8 No. 3, pp. 347-366, Aug. 1, 1998.
Zhang et al, "The hydrolysis of cationic etc." J. Biomaterials 2008 vol. 29, No. 36, Dec. 2008. Abstract, p. 4720, col. 2, para 5, para 6, structure 1, table 1.
Heyes et al, "Antitumor evaluation of a ribonuclease etc." European J. of Cancer 1965, Permagon, vol. 10, No. 7 Jul. 1, 1974. Abstract, p. 431, col. 2 para 2, ph 432 col. 1 Para 1, fig 1.
Parker et al, "Methodologies for monitoring nanoparticle etc." Analytical Biochem. Academic press Inc. NY vol. 302, No. 1, Mar. 1, 2002 pp. 7580, abstract, p. 76, col. 1, para 2.
Abe et al "Contribution of Asian mouse subspecies *Mus musculus molossinus* to genomic constitution . . . " Gene Research vol. 14 No. 12, Jan. 1, 2004. EMBL database Accession No. EMBL AG504103 Jun. 4, 2004. *Mus musculus molossinus* DNA clone MSMg01-405L22.T7 genomic survey sequence.
Arthur et al., "Regulated interactions between partner and non-partner sensors and response regulators that control glycopeptide resistance gene expression in enterococci," *Microbiology*, vol. 145, pp. 1849-1858 (1999).
Barrios et al., Compilation and analysis of σ54-dependent promoter sequences, Nucleic Acids Research, 1999, vol. 27, No. 22, pp. 4305-4313.
Buck et al. Nature. vol. 358, Jul. 30, 1992, p. 422-424.
Choi et al., "Increasing vancomycin susceptibility in vancomycin resistant enterococci by *vanH* promoter and *ddl* transformation," *Journal of Infection*, vol. 48, pp. 314-319 (2004).
Coleman et al., "The Role of Sigma Factors in Regulating Bacterial Stress Responses and Pathogenesis," in Molecular Paradigms of Infectious Disease, A Bacterial Perspective, Nickerson & Schurr, Eds., Springer, Chapter 12, pp. 438-501 (2006).
Cranenburgh et al., "*Escherichia coli* strains that allow antibiotic-free plasmid selection and maintenance by repressor titration," *Nucleic Acids Research*, 2001, vol. 29, No. 5 e26, Oxford University Press, XP-002514866.
Dapa et al., "Multiple Factors Modulate Biofilm Formation by the Anaerobic Pathogen *Clostridium difficile*," Journal of Bacteriology, vol. 195(3), pp. 545-555 (Feb. 2013), with additional data from online version.
Dawson et al., "Characterisation of *Clostridium difficile* Biofilm Formation, a Role for Spo0A," PLOS One, vol. 7(12), pp. 1-13 (Dec. 2012), with additional data from online version.
Deakin et al., "The *Clostridium difficile* spo0A Gene Is a Persistence and Transmission Factor," Infection and Immunity, vol. 80(8), pp. 2704-2711 (Aug. 2012), with additional data from online version.
International Search Report and Written Opinion of the International Searching Authority for PCT/GB2014/050752, mailed on Jun. 16, 2014.
Leang et al., "Genome-wide analysis of the RpoN regulon in *Geobacter sulfurreducens*", BMC Genomics, Biomed Central, London, GB, vol. 10, No. 1, Jul. 22, 2009, p. 331, XP021056141.
Lee et al., "Advantages of the Circular Dumbbell Decoy in Gene Therapy and Studies of Gene Regulation," *Current Drug Targets*, vol. 4, pp. 619-623 (2003).
Mann, "Transcription Factor Decoys: A New Model for Disease Intervention", Annals of the New York Academy of Sciences, vol. 1058, No. 1, Nov. 1, 2005, pp. 128-139, XP55001514.
McArthur et al. "Manipulating and understanding antibiotic production in *Streptomyces coelicolor* A3(2) with decoy oligonucleotides," PNAS, vol. 105(3), pp. 1020-1025 (Jan. 22, 2008).
Morishita et al., "Application of Transcription Factor "Decoy" Strategy as Means of Gene Therapy," *Circulation Research*, 1998, vol. 82, pp. 1023-1028.
Norris et al., "Prokaryotic gene therapy to combat multidrug resistant bacterial infection," *Gene Therapy*, 2000, 723-725, vol. 7, XP009004366.
Onizuka et al., "$CO_2$ response for expression of ribulose-1,5-bisphosphate carboxylase/oxygenase genes is inhibited by AT-rich decoy in the cyanobacterium," *FEBS Letters*, FEBS 27178, 2003, pp. 42-46, vol. 542.
Patil et al., "DNA-based Therapeutics and DNA Delivery Systems: A Comprehensive Review," *The AAPS Journal*, vol. 7(1), Article 9, pp. E61-E77 (2005).
Rosenbusch et al., "*C. difficile* 630Δerm Spo0A Regulates Sporulation, but Does Not Contribute to Toxin Production, by Direct High-Affinity Binding to Target DNA," PLOS One, vol. 7(10), pp. 1-12 (Oct. 2012), with additional data from online version.
Saujet et al., "The Key Sigma Factor of Transition Phase, SigH, Controls Sporulation, Metabolism, and Virulence Factor Expression in *Clostridium difficile*," Journal of Bacteriology, vol. 193(13), pp. 3186-3196 (Jul. 2011), with additional data from online version.
Sebaihia et al., "The multidrug-resistant human pathogen *Clostridium difficile* has a highly mobile, mosaic genome," Nature Genetics, vol. 18(7), pp. 779-786 (Jul. 2006), with additional data from online version.
Shiraishi et al., "Targeted Delivery of Plasmid DNA into the Nucleus of Cells via Nuclear Localization Signal Peptide Conjugated to DNA Intercalating Bis- and Trisacridines," *Bioconjugate Chem.*, vol. 16, pp. 1112-1116 (2005).
Stabler et al., "Comparative genome and phenotypic analysis of *Clostridium difficile* 027 strains provides insight into the evolution of a hypervirulent bacterium," Genome Biology, vol. 10(9), pp. R102-R102.15 (2009), with additional data from online version.
Toledano et al., "Redox-Dependent Shift of OxyR-DNA Contacts along an Extended DNA-Binding Site: A Mechanism for Differential Promoter Selection," *Cell*, Sep. 9, 1994, pp. 897-909, vol. 78, XP024246465.
Torres Viera et al., "Restoration of Vancomycin Susceptibility in *Enterococcus faecalis* by Antiresistance Determinant Gene Transfer," *Antimicrobial Agents and Chemotherapy*, vol. 45(3), pp. 973-975 (Mar. 2001).
Underwood et al., "Characterization of the Sporulation Initiation Pathway of *Clostridium difficile* and Its Role in Toxin Production," Journal of Bacteriology, vol. 191(23), pp. 7296-7305 (Dec. 2009), with additional data from online version.
Weissig et al., "DQAsomes: A Novel Potential Drug and Gene Delivery System Made from Dequalinium™," *Pharmaceutical Res.*, vol. 15(2), pp. 334-337 (1998).
Weissig et al., "Cationic bolasomes with delocalized charge centers as mitochondria-specific DNA delivery systems," *Advanced Drug Delivery Reviews*, vol. 49, pp. 127-149 (2001).

* cited by examiner

NUCLEIC ACID COMPLEXES

This application claims priority to and the benefit of applications No. 1002413.1 (GB) and 61/304,087 (US), both filed 12 Feb. 2012, both of which are hereby incorporated by reference to the fullest extent allowed by law.

A sequence listing text (.txt) file is submitted herewith under 37 CFR. 1.821(c) and is hereby incorporated by reference in its entirely. The details of the file as required under See 37 CFR. 1.52(e)(5) and 37 CFR 1.77(b)(5) are as follows: name of file is "BOXALL_PBL_P003US_SEQ_.txt"; date of creation is 8 Aug. 2012; size is 9017 bytes.

The present invention relates to complexes of nucleic acid sequences. In particular, the present invention relates to complexes of transcription factor decoys, their delivery to bacteria and their formulation.

Control of bacterial growth and virulence poses an increasing problem, particularly in medical and veterinary applications, and may become a major challenge to public health. Antibiotics for use against pathogenic bacteria are well known in the art. However, extensive use of such antibiotics has led to the emergence of bacteria which are resistant to at least one, and in some cases, multiple antibiotics (so-called multi-drug resistant strains). The situation is exacerbated by a decrease in the numbers of conventional antibiotics being discovered and under development. Indeed, antibiotic resistance is a major challenge for antibacterial research and threatens the potency of marketed antibiotics as well as those still under development. Consequently there is a need for new anti-bacterial agents which can be used to tackle bacterial spread and infection.

DNA-based therapies have the potential to overcome the limitations of existing antibacterial therapies because they can be designed to treat potentially any pathogen either by preventing expression of genes encoding an antibiotic resistance mechanism or by inhibiting growth by modifying the expression of essential or adaptive genes or operons or similarly preventing onset of virulence or pathogenicity. In addition, bacteria are unlikely to develop resistance to these agents as this would require simultaneous mutations that affected both the transcription factor and its cognate binding site(s). This is particularly true for agents that control several essential genes. Alternatively a gene could evade transcription factor decoy-mediated control by mutation so that the gene is expressed constitutively. However, in the case of a transcription factor decoy that acts simultaneously on many genes, it would require many of those genes to acquire mutations to switch them to constitutive expression, an event that is considered unlikely.

Transcription Factor Decoys (TFDs) are one such DNA-based therapeutic. Decoy oligonucleotides are designed to mimic the binding sites of transcription factors and prevent the latter from binding to their cognate genomic targets, with a consequent modification of gene expression (Mann and Dzau (2000) *J. Clin. Investigation* 106: 1071-1075).

TFDs have distinct advantages over other DNA-based therapeutics. Their mechanism of action is simple and predictable—they control gene expression by sequestering transcription factors, preventing the latter from binding to promoters by flooding the cell with sufficient copies of the specific binding sequences (hence, the term "decoys"). This is in contrast to antisense strategies where targets are difficult to define due to the complex secondary structure of mRNA. In comparison to antisense approaches, TFDs have the further advantages that they act rapidly, preventing expression of genes, whereas antisense approaches deal with the consequences of expression. As a result, TFDs are effective at much lower concentrations, because a single TFD-transcription factor interaction can block transcription of a single gene that otherwise may have given rise to many thousands of copies of mRNA, which constitute the targets for the antisense approach.

Other DNA-based therapeutics include plasmids containing transgenes for gene therapy, oligonucleotides for antisense and antigene applications (Crooke S. T. (1998) *Antisense Nucleic Acid Drug Dev.* 8: 115-122), ribozymes, DNAzymes, aptamers, and small interfering RNAs (siRNAs) (Stull R. A. et al (1995) *Pharm Res.* 12: 465-483; Patil S. D. and Burgess D. J. (2003) *AAPS Newsmagazine* 6: 27). Although most of the DNA-based drugs are in pre-clinical development or the early stages of clinical trials, this class of compounds has emerged in recent years to yield extremely promising candidates for drug therapy for a wide range of diseases, including cancer, AIDS, neurological disorders such as Parkinson's disease and Alzheimer's disease, and cardiovascular disorders.

However, delivery of DNA-based therapeutics, including TFDs, remains a significant challenge. Cell membranes are one of the major obstacles encountered when delivering large hydrophilic therapeutic agents such as proteins or nucleic acids. Most effort to solve this problem is focused on delivery to eukaryotic cells, to develop effective therapies for human cancer and the like. In eukaryotes the different cellular compartments (including the nucleus) are protected by biological membranes which segregate the various cellular compartments and prevent influx and efflux of solutes from cells and organelles. Although these barriers are essential for the maintenance of the cell, they are a substantial problem when trying to deliver therapeutics to a cell or specific organelles within a cell.

Most cations are unable to pass through cell membranes without specific carrier systems due to the large free energy barrier posed by the hydrophobic interior of the membrane. To be selectively accumulated and retained by a cell, a cationic compound requires sufficient lipophilicity and delocalisation of its positive charges to reduce the free energy change when moving from an aqueous to a hydrophobic environment. This allows the compound to cross the plasma and mitochondrial membranes passively and be accumulated in response to membrane potential.

Transport of proteins into eukaryotic cells is mainly mediated through endocytosis. This is a highly organised transport system in which large polar molecules are absorbed by being engulfed in the cell membrane. Phagocytosis and pinocytosis are non-receptor-mediated forms of endocytosis while receptor-mediated endocytosis is a more specific active event where the cytoplasm membrane folds inward to form coated pits. In this case, proteins or other trigger particles lock into receptors/ligands in the cell's plasma membrane or by non-specific interaction with the surface of the cell, for example due to charge interactions. It is only then that the particles are engulfed. These inward budding vesicles bud to form cytoplasmic vesicles.

Various techniques have been developed to translocate biologically active molecules across these barriers in vivo and in vitro. Electroporation and microinjection are harsh and impractical to use in vivo because these methods necessitate disruption of the cell membrane before substances can be introduced into the cell and therefore they are restricted to a limited amount of cells.

While use of the endocytotic pathway is appealing, one significant drawback is ensuring endosomal escape before lysosomal activity occurs. Liposome encapsulation and receptor-mediated endocytosis are also limited by their lack of targeting and low yield of delivery. Most of the exploratory work carried out to date has focussed on the delivery of siRNA molecules to eukaryotic cells. The approach usually taken is to form liposomes or complexes with covalently attached targeting peptides which direct the therapeutic to the appropriate target within the cell.

There are many considerations when selecting the lipid component for such a delivery mechanism. The lipid-like component is generally cationic and has three functions:
1. to condense the nucleic acid to make delivery more achievable;
2. to protect the nucleic acid from degradation by nucleases or non-specific absorption by plasma proteins etc., and
3. to shield the negative charge of phosphate backbone.

The third point can be overcome by using synthetic backbones with reduced or no charge.

In addition, liposomes or complexes require certain ideal physical properties:
1. Good stability, both in salt or biological fluids. This can be quantified with the $\xi$-potential which measures the attraction or repulsion between the particles;
2. Narrow size distribution, for bacteria ideally between 50 and 100 nm;
3. Lower toxicity, although most transfection agents (lipids, lipophilic cations) show moderate levels of toxicity;
4. Practical to produce, incorporating issues such as cost of goods.

Peptides used for eukaryotic delivery are generally known to permeabilise membranes, to be cell-penetrating via specific receptors on target cells, or simply to be cationic (e.g. poly-arginine). The use of peptides with cell-penetrating properties has several advantages, which are mainly due to the various modifications that can be made to the peptide sequence. This allows the engineering of carriers addressing different cellular subdomains and/or able to transport various types of cargoes.

A class of membrane translocating agents is the cell-penetrating peptides (CPPs). Apart from being a mild and effective tool for access to different cellular organelles in vitro, CPPs have been used for cellular delivery of several agents in vivo, with promising results.

CPPs generally consist of less than 30 amino acids, have a net positive charge and have the ability to translocate the plasma membrane and transport several different cargoes into the cytoplasm and nucleus in a seemingly energy-independent manner. Translocation occurs via an as yet unknown mechanism that is not affected by various endocytosis inhibitors or low temperatures (Lange Ü., ed. (2002) *Cell-Penetrating Peptides, Processes and Applications*, CRC Press).

The term CPP includes synthetic cell-permeable peptides, protein-transduction domains and membrane-translocating sequences, which all have the ability to translocate the cell membrane and gain access to the cellular interior.

Other classes of peptides with the potential to affect delivery especially to bacteria are those with antibacterial properties. These include the Anti-Microbial Peptides (AMPs), cell penetrating peptides (CPPs), those peptides that are synthesised non-ribosomally and glycopeptides. All these types of peptides are referred to herein as Anti-Bacterial Proteins (ABPs).

AMPs can be derived from bacterial sources, where they are referred to as bacteriocins, or from higher eukaryotic sources, including humans, amphibians, insects etc. AMPs of particular interest are those that are able to either increase the permeability of biological membranes or have the ability to translocate across membranes to reach their intracellular targets. AMPs are generally divided into five non-mutually exclusive sub-groups on the basis of structural similarities (Brogden, 2005 Nat. Rev. Microbiol. 3: 238-250):
1. Anionic peptides are small peptides commonly complexed with zinc and active against Gram-negative and Gram-positive bacteria;
2. Linear cationic α-helical peptides (such as buforin) that are less than 40 amino acids in length, lack cysteines and feature a central hinge region between two alpha-helical regions;
3. Cationic peptides that are enriched for specific amino acids, such as proline- and arginine-rich apidaecins;
4. Anionic and cationic peptides that form beta-sheets due to formation of disulphide bonds between cysteine groups;
5. Anionic and cationic peptides that are fragments of larger proteins.

The mechanisms by which the AMPs affect microbial killing are varied and not confined to certain sub-groups. The majority kill bacteria by forming pores in their membranes leading to the cells being permeabilised. There are thought to be three distinct mechanisms of permeabilisation, which can either be a specific property of a peptide or an effect of the concentration of the peptide used:
1. Formation of torroidal pores by, for example, magainin, melittin;
2. Carpet formation by, for example, dermaseptin S, cecropin or melittin;
3. Barrel stave formation by, for example, alamethicin.

Several AMPs have been described where the final target is not the membrane but intracellular in nature, necessitating that the AMP translocates across the membrane. This ability to translocate is of particular interest as these peptides, or synthetic peptides modelled on them, could be used to deliver alternative cargoes such as therapeutics. These AMPs can therefore be classed according to their modes of intracellular killing:
1. Binding of nucleic acids by, for example, buforin, buforin II and analogues and tachyplesin;
2. Flocculation of intracellular contents by, for example, anionic peptides;
3. Septum formation by, for example, microcin 25;
4. Cell wall synthesis by, for example, mersacidin;
5. Inhibition of nucleic-acid synthesis by, for example, pleurocidin and dermaseptin;
6. Inhibition of protein synthesis by, for example, pleurocidin and dermaseptin;
7. Inhibition of enzymatic activity by, for example, apidaecins.

Non-ribosomally synthesised peptides can be structurally diverse. They are often cyclised or branched, contain non-standard amino acids or amino acids that have been modified to produce hydroxyalanine or hydroxyserine, and can be subject to hydroxylation, halogenation or glycosylation (Walsh et al (2004) *Science* 303: 1805-1810). The majority of these peptides inhibit growth of bacteria by permeabilising their membranes.

The challenges of peptide and nucleic acid delivery to bacteria are similar to those encountered with eukaryotic cells but the cellular components are different. In particular, bacteria do not have an endocytic mechanism to help moving the therapeutic into the cell. However, a clear advantage is that bacteria do not have a nuclear compartment so it is sufficient to deliver the therapeutic into the cytoplasm for it to gain access to the bacterial genome. Therefore, alternatives to eukaryotic delivery systems need to be developed. These involve finding ways of gaining entry to the cell by permeabilising the membrane(s). In a laboratory setting, delivery of DNA into cells (transfection) is achieved by either treating the cells with anionic buffers that disrupt the cell membranes by interfering with charge distribution, most commonly by buffers containing calcium ions. Alternatively electroporation is used, where cells are prepared in buffers with low conductance and high voltages are used to produce transient pores in the bacterial membranes of some of the cells, though by no means all, resulting in transfection of a minority of the cells.

It is evidently impractical to use either method to deliver DNA therapeutics to bacteria either in animal models or in a clinical setting. Transfection in vivo may be achieved by conjugating the therapeutic to a synthetic cationic peptide or ABP known to damage the membranes and cause entry through the subsequent pores or extrusions. Additionally the ability of some of the ABPs to translocate through membranes is another alternative in developing a credible delivery strategy.

Starting from the eukaryotic model of using delivery peptides, ideal features for bacterial delivery peptides include:
1. bacterial-specificity/preference, being optimised for prokaryotes rather than eukaryotes;
2. low likelihood of eliciting resistance. Cationic peptides, for example, can be resisted by MRSA which alters the charge density of its outer membrane;
3. broad-spectrum activity so for use as a general delivery system to bacteria; and
4. low or no host toxicity.

Similarly, the use of lipid-like transport molecules needs to be tailored to the specific construction of bacterial membrane. For example, Gram-negative bacteria have an outer and an inner membrane, both of which need to be overcome before the therapeutic is delivered into the bacterium.

Against this background, the present invention provides a solution for the formulation and delivery of nucleic acid sequences, such as TFDs, to bacteria.

Specifically, the present invention resides in an antibacterial complex comprising a nucleic acid sequence and one or more delivery moieties. The inventors have found that delivery moieties that have some antibacterial activity in their own right are ideal. In particular, the delivery moiety or moieties should show a synergistic antibacterial effect when combined with the nucleic acid sequence. In other words, the combination of the delivery moiety and the nucleic acid sequence should show an enhanced antibacterial effect when compared to the effect of the nucleic acid sequence or delivery moiety alone.

The delivery moiety may be selected from quaternary amine compounds and bis-aminoalkanes and unsaturated derivatives thereof, wherein the term "aminoalkanes" as used herein refers to amino groups (preferably tertiary amino groups) that form part of a heterocyclic ring.

Exemplary of such compounds are compounds of the formula (I):

wherein Q is selected from:
(a) a group $Q^1$ having the formula:

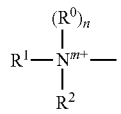

and
(b) a group $Q^2$, $Q^2$-NH—, $Q^2$-O—, or $Q^2$-S— wherein $Q^2$ is selected from monocyclic, bicyclic and tricyclic heteroaromatic groups of 5 to 14 ring members, of which 1, 2 or 3 are heteroatom ring members selected from N, O and S provided that at least one nitrogen ring member is present, wherein the heteroaromatic groups are optionally substituted by one or two substituents $R^{4a}$ and wherein the said one nitrogen ring member may form an N-oxide or may be substituted with $C_{1-4}$ alkyl, phenyl-$C_{1-4}$ alkyl or di-phenyl-$C_{1-4}$ alkyl to form a quaternary group, wherein the phenyl moieties in each case are optionally substituted with one or two halogen, methyl or methoxy groups;

m is 0 or 1;

n is 0 or 1;

p and q are the same or different and each is an integer from 1 to 12;

A is a bond or is selected from a naphthalene, biphenyl, terphenyl, phenanthrene, fluorene, stilbene, a group $C_6H_4(CH_2)_rC_6H_4$, a group $C_6H_4$—C≡C—$C_6H_4$, a pyridine-2,6-diyl-bis(benzene-1,4-diyl) group, a group CH═CH—$(CH_2)_s$—(CH═CH)$_t$—; and a group C≡C—$(CH_2)_u$—(C≡C)$_v$—; wherein r is 0-4, s is 0 to 4, t is 0 or 1; u is 0-4 and v is 0 or 1;

when n is 1, $R^0$, $R^1$ and $R^2$ are each selected from $C_{1-4}$ alkyl; and when n is 0, then N, $R^1$ and $R^2$ together form a monocyclic, bicyclic or tricyclic heteroaromatic group of 5 to 14 ring members, of which one is the nitrogen atom N and 0, 1 or 2 are further heteroatom ring members selected from N, O and S, and wherein the heteroaromatic group is optionally substituted by one or two substituents $R^{4b}$; and $R^3$ is selected from hydrogen, $C_{1-4}$ alkyl, halogen, monocyclic carbocyclic groups of 3 to 7 ring members each optionally substituted by one or two substituents $R^{4c}$, a group Q; a group —NH-$Q^2$, a group —O-$Q^2$ and a group —S-$Q^2$; and $R^{4a}$, $R^{4b}$ and $R^{4c}$ are the same or different and each is selected from $C_{1-4}$ alkyl optionally substituted with one or more fluorine atoms; $C_{1-4}$ alkoxy optionally substituted with one or more fluorine atoms; nitro; amino; mono- and di-$C_{1-4}$ alkylamino; halogen; phenyl-$C_{1-2}$ alkyl wherein the phenyl moiety is optionally substituted with one or two methoxy, methyl or halogen substituents; ureido and guanidinyl.

In one preferred embodiment, Q is a group $Q^1$:

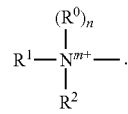

Accordingly, one preferred sub-group of compounds within formula (I) is represented by formula (II):

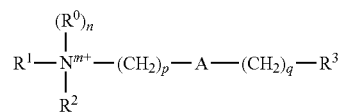

wherein $R^1$, $R^2$, m, p, A, q and $R^3$ are as defined in respect of formula (I).

One preferred sub-group of compounds within formula (II), wherein $R^3$ is $Q^1$ and n in each instance is 0, can be represented by the formula (III):

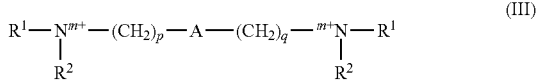

wherein $R^1$, $R^2$, m, p, A and q are as defined in respect of formula (I).

In the compounds of formulae (I), (II) and (III), when m is 1, the nitrogen atom N must be a quaternary nitrogen. Accordingly, the compounds of formulae (I), (II) and (III) wherein m is 1 will comprise one or more anions as counter ions, for example anions derived from mineral acids, sulphonic acids and carboxylic acids.

When N, $R^1$ and $R^2$ together form a monocyclic, bicyclic or tricyclic heteroaromatic group of 5 to 14 ring members, typically the group contains either the nitrogen atom N as the sole heteroatom ring member or contains a second heteroatom ring member selected from N, O and S.

When N, $R^1$ and $R^2$ together form a monocyclic, bicyclic or tricyclic heteroaromatic group, the nitrogen atom N forms part of an aromatic ring. Preferred heteroaromatic groups are monocyclic aromatic rings; bicyclic heterocyclic rings in which both rings are aromatic; bicyclic heterocyclic rings in which one nitrogen-containing ring is aromatic and the other ring is non-aromatic; and tricyclic rings in which two rings, including a nitrogen-containing ring, are aromatic and the other ring is non-aromatic.

When N, $R^1$ and $R^2$ together form a monocyclic, bicyclic or tricyclic heterocyclic group of 5 to 14 ring members, the heterocyclic group is preferably selected from quinoline; isoquinoline; acridine; tetrahydroacridine and ring homologues thereof; pyridine; benzoimidazole; benzoxazole and benzothiazole. By ring homologues of tetrahydroacridine is meant compounds containing the core structure:

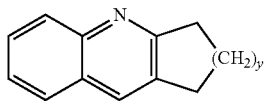

wherein y is 1 or 3. By tetrahydroacridine is meant a compound having the core structure above wherein y is 2.

In a preferred embodiment, the delivery moiety is a quaternary derivative of quinoline or acridine, in particular 1,2,3,4-tetra-hydro-9-amino-acridine. Suitable derivatives of 1,2,3,4-tetra-hydro-9-amino-acridine are described in U.S. Pat. No. 3,519,631, the contents of which are incorporated herein by reference. Of particular interest are the compounds and formulae exemplified in Examples 17 to 25 of U.S. Pat. No. 3,519,631 and analogues thereof. Suitable quinoline derivatives are the bis-quinolinium compounds, such as dequalinium, and analogues thereof.

Dequalinium (FIG. 1) is a bis-quinolinium compound, has mild antimicrobial properties and has been used for 30 years as an antimicrobial agent in over-the-counter mouthwashes, topical ointments, oral and vaginal paints, and sore-throat lozenges. It is a topical bacteriostat and has also been tested as an inhibitor of calcium channels, an antifungal agent (Ng et al. (2007) Bioorg. Medicinal Chem. 15: 3422-3429), an inhibitor of Tuberculosis (Guiterrez-Lugo et al. (2009) J. Biomol. Screen. 14: 643-652) and as an inhibitor of Protein Kinase C (PKC; Abeywickrama et al. (2006) Bioorg. Medicinal Chem. 14: 7796-7803).

Dequalinium has also been used to deliver DNA-based therapeutics and conventional drugs, such as paxcitol, to mitochondria in in vitro experiments. In these experiments, dequalinium was prepared as bolasomes by the dry-film method. That is, dequalinium is dissolved in an organic solvent, such as methanol, dried to completion in a vacuum and re-suspended in an aqueous solution, whereupon it is sonicated to form bolasomes which are subsequently mixed with DNA to form complexes. These complexes have been shown to be capable of delivering DNA to mitochondria by a mechanism which is believed to involve fusion of the complexes with the outer membrane of the mitochondria (Weissig and Torchilin 2001 Adv. Drug Delivery Rev. 49: 127-149; Weissig et al. 2001 J. Control. Release 75: 401-408). Although the membrane structure of mitochondria is not equivalent to those that occur in bacteria, it is similar. This raises the possibility that dequalinium could be suitable to deliver therapeutics to bacteria in an in vivo setting. However, the complexes formed with dequalinium are unstable over time in the presence of physiological buffers and biological fluids and to dilution.

Therefore, in a particularly preferred embodiment, the complex comprises a dequalinium analogue. In this way, it is possible to design a dequalinium compound that has enhanced stability (both to dilution and the presence of salt) and yet has a similar or improved toxicity profiles to dequalinium. Such an analogue has been described that forms more stable complexes (Compound 7, Galanakis et al. [J. Med. Chem. (1995) 35: 3536-3546]) as tested by various physiochemical parameters such as ability to bind DNA to the exclusion of fluorescent dye SYBR-green, size of particles formed as measured by Dynamic Light Scattering and visualised with electron microscopy and their stability in elevated concentrations of salt and on dilution and storage for extended periods (Weissig et al. (2001) S. T. P. Pharma Sciences 11: 91-96).

Examples of dequalinium and its analogues are compounds of the formula (IV):

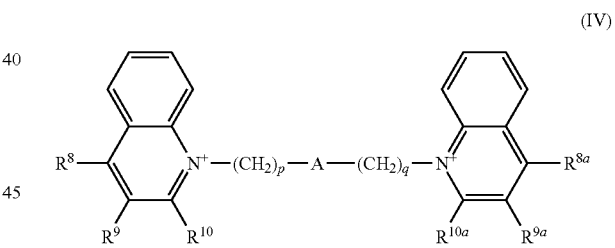

wherein:
p and q are the same or different and each is an integer from 1 to 12;
A is a bond or is selected from naphthalene, biphenyl, terphenyl, phenanthrene, fluorene, stilbene, a group $C_6H_4(CH_2)_r$ $C_6H_4$, a group $C_6H_4$—C≡C—$_6H_4$, a pyridine-2,6-diyl-bis (benzene-1,4-diyl) group, a group CH=CH—$(CH_2)_s$—(CH=CH)$_t$—; and a group C≡C—$(CH_2)_u$—(C≡C)$_v$—; wherein r is 0-4, s is 0 to 4, t is 0 or 1; u is 0-4 and v is 0 or 1;
$R^8$, $R^9$ and $R^{10}$ are the same or different and are each selected from hydrogen; $C_{1-4}$ alkyl optionally substituted with one or more fluorine atoms; $C_{1-4}$ alkoxy optionally substituted with one or more fluorine atoms; nitro; amino; mono- and di-$C_{1-4}$ alkylamino; halogen, phenyl-$C_{1-2}$ alkyl wherein the phenyl moiety is optionally substituted with one or two methoxy, methyl or halogen substituents; ureido and guanidinyl; or $R^9$ and $R^{10}$ link together to form an alkylene chain $(CH_2)_w$ wherein w is 3 to 5; and $R^{8a}$, $R^{9a}$ and $R^{10a}$ are the same or different and are each selected from hydrogen; $C_{1-4}$ alkyl optionally substituted with one or more fluorine atoms: $C_{1-4}$ alkoxy optionally substituted with one or more fluorine atoms; nitro; amino; mono- and di-$C_{1-4}$ alkylamino; halogen, phenyl-$C_{1-2}$ alkyl wherein the phenyl moiety is optionally substituted with one or two methoxy, methyl or halogen substituents; ureido and guanidinyl; or $R^{9a}$ and $R^{10a}$ link together to form an alkylene chain $(CH_2)_w$ wherein w is 3 to 5.

Within formula (IV), one subset of compounds is the subset in which A is a bond, a group $CH=CH-(CH_2)_s-(CH=CH)_t-$; or a group $C\equiv C-(CH_2)_u-(C\equiv C)_v-$. Within this sub-set, preferably A is a bond, i.e. there is a saturated alkylene chain extending between the nitrogen atoms of the two quinoline rings.

When A is a bond, typically the sum of p and q is in the range from 3 to 22, preferably in the range from 6 to 20, and more preferably from 8 to 18. Particular examples are compounds in which p+q=8, or p+q=9, or p+q=10, or p+q=11, or p+q=12, or p+q=13, or p+q=14, or p+q=15, or p+q=16, or p+q=17 or p+q=18.

In each of the foregoing embodiments and subsets of compounds, $R^8$ and $R^{8a}$ are preferably each selected from hydrogen; $C_{1-4}$ alkoxy; nitro; amino; mono- and di-$C_{1-4}$ alkylamino; and guanidinyl.

More preferably, $R^8$ and $R^{8a}$ are each selected from hydrogen; $C_{1-4}$ alkoxy; amino and guanidinyl.

Still more preferably, $R^8$ and $R^{8a}$ are each selected from methoxy and amino.

In one embodiment, $R^8$ and $R^{8a}$ are both amino.

In another embodiment, $R^8$ and $R^{8a}$ are both methoxy.

In another embodiment, $R^8$ and $R^{8a}$ are both guanidinyl.

In each of the foregoing embodiments and subsets of compounds, preferably:

$R^9$ is hydrogen;
$R^{9a}$ is hydrogen;
$R^{10}$ is selected from hydrogen; amino; and $C_{1-4}$ alkyl optionally substituted with one or more fluorine atoms;
$R^{10a}$ is selected from hydrogen; amino; and $C_{1-4}$ alkyl optionally substituted with one or more fluorine atoms;
or $R^9$ and $R''$ link together to form an alkylene chain $(CH_2)_w$ wherein w is 3 to 5: and/or
$R^{9a}$ and $R^{10a}$ link together to form an alkylene chain $(CH_2)_w$ wherein w is 3 to 5.

More preferably:
$R^9$ is hydrogen;
$R^{9a}$ is hydrogen;
$R^{10}$ is selected from hydrogen; amino; methyl and trifluoromethyl;
$R^{10a}$ is selected from hydrogen; amino; methyl and trifluoromethyl;
or $R^9$ and $R^{10}$ link together to form an alkylene chain $(CH_2)_w$ wherein w is 3 to 5: and/or
$R^{9a}$ and $R^{10a}$ link together to form an alkylene chain $(CH_2)_w$ wherein w is 3 to 5.

In one particularly preferred group of compounds within formula (IV):
A is a bond;
the sum of p and q is in the range from 8 to 18;
$R^8$ and $R^{8a}$ are each selected from hydrogen; $C_{1-4}$ alkoxy; amino and guanidinyl;
$R^9$ is hydrogen;
$R^{9a}$ is hydrogen;
$R^{10}$ is selected from hydrogen; amino; and $C_{1-4}$ alkyl optionally substituted with one or more fluorine atoms;
$R^{10a}$ is selected from hydrogen; amino; and $C_{1-4}$ alkyl optionally substituted with one or more fluorine atoms;
or $R^9$ and $R^{10}$ link together to form an alkylene chain $(CH_2)_w$ wherein w is 3 to 5: and/or
$R^{9a}$ and $R^{10a}$ link together to form an alkylene chain $(CH_2)_w$ wherein w is 3 to 5.

In another particularly preferred group of compounds within formula (IV):
A is a bond;
the sum of p and q is in the range from 8 to 18;
$R^8$ and $R^{8a}$ are each guanidinyl;
$R^9$ is hydrogen;
$R^{9a}$ is hydrogen;
$R^{10}$ is selected from hydrogen; amino; and $C_{1-4}$ alkyl optionally substituted with one or more fluorine atoms;
$R^{10a}$ is selected from hydrogen; amino; and $C_{1-4}$ alkyl optionally substituted with one or more fluorine atoms;
or $R^9$ and $R^{10}$ link together to form an alkylene chain $(CH_2)_w$ wherein w is 3 to 5: and/or
$R^{9a}$ and $R^{10a}$ link together to form an alkylene chain $(CH_2)_w$ wherein w is 3 to 5.

In another particularly preferred group of compounds within formula (IV):
A is a bond;
the sum of p and q is in the range from 8 to 18;
$R^8$ and $R^{8a}$ are each selected from hydrogen; $C_{1-4}$ alkoxy and amino;
$R^9$ is hydrogen;
$R^{9a}$ is hydrogen;
$R^{10}$ is selected from hydrogen; amino; and $C_{1-4}$ alkyl optionally substituted with one or more fluorine atoms;
$R^{10a}$ is selected from hydrogen; amino; and $C_{1-4}$ alkyl optionally substituted with one or more fluorine atoms;
or $R^{9a}$ and $R^{10a}$ link together to form an alkylene chain $(CH_2)_w$ wherein w is 3 to 5: and/or
$R^{9a}$ and $R^{10a}$ link together to form an alkylene chain $(CH_2)_w$ wherein w is 3 to 5.

Within this group, more preferred compounds are those in which:
A is a bond;
the sum of p and q is in the range from 8 to 18;
$R^8$ and $R^{8a}$ are each selected from hydrogen; methoxy and amino;
$R^9$ is hydrogen;
$R^{9a}$ is hydrogen;
$R^{10}$ is selected from hydrogen; amino; methyl; and trifluoromethyl;
$R^{10a}$ is selected from hydrogen; amino; methyl; and trifluoromethyl;
or $R^9$ and $R^{10}$ link together to form an alkylene chain $(CH_2)_w$ wherein w is 3 to 5: and/or
$R^{9a}$ and $R^{10a}$ link together to form an alkylene chain $(CH_2)_w$ wherein w is 3 to 5.

Within formula (IV), one preferred group of compounds may be represented by the formula (V):

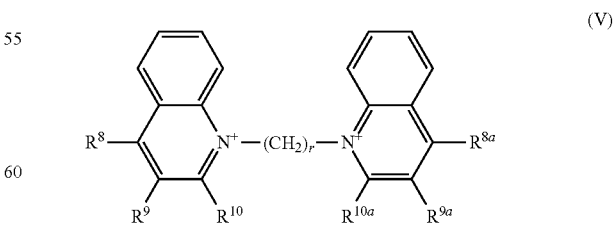

(V)

wherein:
r is an integer from 2 to 24;
$R^8$, $R^9$ and $R^{10}$ are the same or different and are each selected from hydrogen; $C_{1-4}$ alkyl optionally substituted with one or more fluorine atoms: $C_{1-4}$ alkoxy optionally substituted with one or more fluorine atoms; nitro; amino; mono- and di-$C_{1-4}$ alkylamino; halogen, phenyl-$C_{1-2}$ alkyl wherein the phenyl moiety is optionally substituted with one or two methoxy, methyl or halogen substituents; ureido and guanidinyl; or $R^9$ and $R^{10}$ link together to form an alkylene chain $(CH_2)_w$ wherein w is 3 to 5; and $R^{8a}$, $R^{9a}$ and $R^{10a}$ are the same or different and are each selected from hydrogen; $C_{1-4}$ alkyl optionally substituted with one or more fluorine atoms: $C_{1-4}$ alkoxy optionally substituted with one or more fluorine atoms; nitro; amino; mono- and di-$C_{1-4}$ alkylamino; halogen, phenyl-$C_{1-2}$ alkyl wherein the phenyl moiety is optionally substituted with one or two methoxy, methyl or halogen substituents; ureido and guanidinyl; or $R^{9a}$ and $R^{10a}$ link together to form an alkylene chain $(CH_2)_w$ wherein w is 3 to 5; provided that:

(i) when $R^{10}$ and $R^{10a}$ are both hydrogen or are both methyl, and $R^9$ and $R^{9a}$ are both hydrogen, then at least one of $R^8$ and $R^{8a}$ is other than hydrogen, amino or dimethylamino; and (ii) when $R^9$ and $R^{10}$ link together to form an alkylene chain $(CH_2)_w$ wherein w is 4 and $R^{9a}$ and $R^{10a}$ link together to form an alkylene chain $(CH_2)_w$ wherein w is 4, then at least one of $R^8$ and $R^{8a}$ is other than amino.

Preferably, r is an integer from 8 to 20, more preferably 10 to 18, for example any one of 10, 12, 13, 14, 15, 16, 17 and 18.

In one group of compounds within formula (V), $R^8$ and $R^{8a}$ are selected from methoxy and guanidinyl. Within this group of compounds, $R^9$ and $R^{9a}$ typically are both hydrogen and $R^{10}$ and $R^{10a}$ typically are selected from hydrogen, methyl, trifluoromethyl and amino.

In another group of compounds within formula (V), $R^8$ and $R^{8a}$ are selected from hydrogen, amino, mono- and di-$C_{1-4}$ alkylamino; methoxy and guanidinyl; $R^9$ and $R^{9a}$ are both hydrogen and $R^{10}$ and $R^{10a}$ are both trifluoromethyl.

Figure 2:
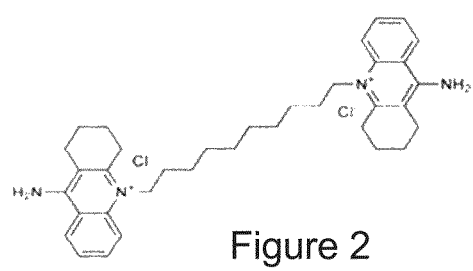

In another embodiment, the analogue may be 10,10'-(decane-1,10-diyl)bis(9-amino-1,2,3,4-tetrahydroacridinium) dichloride (FIG. 2). This compound is referred to in this specification as Compound 7 because of its original notation in Galanakis et al. (*J. Med. Chem.* (1995) 35: 3536-3546) where it was being investigated as a potential inhibitor of calcium channels. The compound has subsequently been tested as an agent for delivery of DNA therapeutics to mitochondria (Weissig et al. (2001) *S. T. P. Pharma Sci.* 11: 91-96) in which publication the advantageous stability of the complexes formed by the Compound 7 analogue were reported. A further paper (Weissig et al. (2006) *J. Liposome Res.* 16: 249-264) reported that the Compound 7 analogue has lower toxicity in vitro compared to dequalinium.

As analogues of dequalinium with longer alkyl chains showed even lower toxicity, analogues with different chain lengths were considered (Weissig et al. (2006) *J. Liposome Res.* 16: 249-264). Thus, preferably, the alkyl chain of the dequalinium analogue has between 8 and 14 methyl groups, but with examples of chains containing as few as 3 methyl groups (Galankis et al (1996) *J. Med. Chem.* 39: 3592-3595) and other lipophilic cations containing as many as 36 methyl groups in the alkyl chain (Eaton et al. (2000) *Angew. Chem. Int. Ed.* 39: 4063-4067). More preferably, the alkyl chain has 10 or 12 methyl groups. As a result, an analogue of Compound 7 was designed with a 12 methyl groups in the alkyl chain, referred to herein after as Compound 7_12.

Another suitable analogue is 10,10'-(dodecane-1,12-diyl) bis(9-amino-1,2,3,4-tetrahydroacridinium)dichloride (FIG. 3) denoted hereinafter as Compound 7_12. Compound 7_12 is derived from Compound 7 and has a C12 alkyl chain, rather than the C10 alkyl chain of Compound 7.

Other suitable analogues of dequalinium include:
1-decanyl-2-methyl-4-aminoquinolinium iodide
1-butyl-2-methyl-4-aminoquinolinium iodide
1,1,1-triethyl-1-(10-iododecan-1-yl)ammonium iodide
1-[1-(N,N,N-triethylammonium-1-yl)-2-methyl-4-aminoquinolinium diiodide
1,1'-(decane-1,10-diyl)bis(4-aminopyridinium)diiodide
1-(4-pentyn-1-yl)-4-aminopyridinium chloride
1,1'-(deca-4,6-diyne-1,10-diyl)bis(4-aminopyridinium) dichloride dehydrate
2,2'-N,N'-(decane-1,10-diyl)bis(2,4-diaminopyridine) [compound 8]
2,2'-N,N'-(decane-1,10-diyl)bis(2-aminopyridine)
2,2'-N,N'-(decane-1,10-diyl)bis(1-methyl-2-aminopyridinium)diiodide
1-(4-pentyn-1-yl)-2-methyl-4-aminoquinolinium iodide
1,1'-(deca-4,6-diyne-1,10-diyl)bis(4-amino-2-methylquinolinium)diiodide hydrate
1,1'-(decane-1,10-diyl)bis(quinolinium)diiodide
1,1'-(decane-1,10-diyl)bis(9-amino-1,2,3,4-tetra-hydroacridinium)dibromide hydrate
2,2'-(decane-1,10-diyl)bis(quinoline)
2,2'-(decane-1,10-diyl)bis(1-methylquinolinium)diiodide hydrate
2,2'-(decane-1,10-diyl)bis(4-methoxyquinoline)
2,2'-(decane-1,10-diyl)bis(1-methyl-4-methoxyquinolinium)diiodide
2,2'-(dodecane-1,12-diyl)bis(1-methylquinolinium)diiodide
2,2'-(decane-1,10-diyl)bis(isoquinolinium)diiodide
1,1'-(decane-1,10-diyl)bis(4-bromoisoquinolinium)diiodide
1,1'-(decane-1,10-diyl)bis(1H-benzimidazole)
1,1'-(decane-1,10-diyl)bis(3-methylbenzimidazolium)diiodide hemihydrate
1,1'-(decane-1,10-diyl)bis(2-methylbenzimidazole)
1,1'-(decane-1,10-diyl)bis(2,3-dimethylbenzimidazolium) diiodide
1,10-bis[N-(acridin-9-yl)amino]decane dihydrochloride dihydrate
1,1'-(1,10-Decanediyl)bis[4-amino-2-methyl quinolinium] diiodide
1,1'-(1,10-Decanediyl)bis[4-aminoquinolinium]diiodide
1,1'-(1,10-Decanediyl)bis[4-N,N,dimethylaminoquinolinium]diiodide
1,1'-(1,10-Decanediyl)bis[2-methylquinolinium]diiodide
1,1'-(1,10-Decanediyl)bis[quinolinium]diiodide
1,6-Bis[N-(1-methylquinolinium-2-methyl)amino]hexane diiodide
1,1'-(1,10-Decanediyl)bis[1-amino isoquinolinium]diiodide
1,1'-(1,10-Decanediyl)bis[2-methylbenzoxazolium]diiodide
1,1'-(1,10-Decanediyl)bis[2-methylbenzothiazolium]diiodide
1,1'-(1,10-Decanediyl)bis[2-amino-1-methylbenzimidazolium]diiodide
1,1'-[(E)-5-Decene-1,10-diyl]bis[4-amino-2-methylquinolinium], diiodide
1,1'-[(Z)-5-Decene-1,10-diyl]bis[4-amino-2-methylquinolinium], diiodide
1,1'-(1,12-Dodecanediyl)bis[4-amino-2-methylquinolinium], diiodide
1,1'-(1,14-Tetradecanediyl)bis[4-amino-2-methylquinolinium], diiodide
1,1'-(1,16-Hexadecanediyl)bis[4-amino-2-methylquinolinium], diiodide
N-Decyl-4-aminoquinaldinium Iodide
1,1'-[Biphenyl-3,3'-diylbis(methylene)]-bis(4-aminoquinolinium)

Dibromide Hydrate (4), 1,1'-[Biphenyl-4,4'-diylbis(methylene)]bis(4-aminoquinolinium)Ditrifluoroacetate
1,1'-(Phenanthrene-3,6-diylbis(methylene)]bis(4-aminoquinolinium)Dibromide Hydrate Ethanoate
1,1'-[Fluorene-2,7-diylbis(methylene)]-bis(4-aminoquinolinium)Ditrifluoroacetate
1,1'-[Methylenebis(benzene-1,4-diylmethylene)]bis(4-aminoquinolinium)Dibromide Hydrate
1,1'-[Ethylenebis-(benzene-1,4-diylmethylene)]bis(4-aminoquinolinium)Dibromide Hydrate
(Z)-1,1'-[Stilbene-4,4'-diylbis(methylene)]-bis(4-aminoquinolinium)Dibromide Sesquihydrate
(E)-1,1'[Stilbene-4,4'-diylbis(methylene)]bis-(4-aminoquinolinium)Dibromide Dihydrate
1,1'-[Ethyne-1,2-diylbis(benzene-1,4-diylmethylene)]bis(4-aminoquinolinium)Dibromide Sesquihydrate
1,1'-[Propane-1,3-diylbis(benzene-1,4-diylmethylene)]bis(4-aminoquinolinium)Dibromide Hemihydrate Ethanoate
1,1'-[Pyridine-2,6-diylbis(benzene-1,4-diylmethylene)]-bis(4-aminoquinolinium)Dibromide Hydrate
1,1'-[Butane-1,4-diylbis(benzene-1,4-diylmethylene)]bis-(4-aminoquinolinium)Dibromide Hydrate
1,1'-[1,1:4',1''-Terphenyl-4,4''-diylbis(methylene)]bis(4-aminoquinolinium)Dibromide Trihydrate
1,1'-[Naphthalene-2,6-diyl(bis(methylene)]bis(4-aminoquinolinium)Dibromide Hydrate
1,1'-[Benzene-1,4-diylbis(methylene)]-bis(4-aminoquinolinium)Dibromide Dihydrate
1,1'-[Benzene-1,3-diylbis(methylene)]bis(4-aminoquinolinium)Dibromide Hemihydrate
1,1'-(Propane-1,3-diyl)bis(4-aminoquinolinium)diiodide
1,1'-(Butane-1,4-diyl)bis(4-aminoquinolinium)diiodide
1,1'-(Pentane-1,5-diyl)bis(4-aminoquinolinium)diiodide
1,1'-(Hexane-1,6-diyl)bis(4-aminoquinolinium)diiodide
1,1'-(Octane-1,8-diyl)bis(4-aminoquinolinium)diiodide
1,1'-(Dodecane-1,12-diyl)bis(4-aminoquinolinium)dibromide hemihydrate
1,10-Bis[N-(2-methylquinolin-4-yl)amino]decane
1,12-Bis[N-(2-methylquinolin-4-yl)amino]dodecane
1,10-Bis[(2-methylquinolin-4-yl)amino]decane
1,12-Bis[(2-methylquinolin-4-yl)amino]dodecane
1,10-Bis(N-quinolin-4-ylamino)decane
4,4'-[Decane-1,10-diylbis(oxy)]bis[quinoline]
4,4'-[Decane-1,10-diylbis(thio)]bis[quinoline]
4,4'-Dodecane-1,12-diylbis[quinoline]
1,8-Bis(N-quinolin-4-yldiamino)octane
1,8-Bis[N-(1-methylquinolinium-4-yl)amino]octane Diiodide Hydrate
1,10-Bis[N-(1-methylquinolinium-4-yl)amino]decane Diiodide
4,4'-[Decane-1,10-diylbis(oxy)]bis[1-methylquinolinium] Diiodide
4,4'-[Decane-1,10-diylbis(thio)]bis[1-methylquinolinium] Diiodide Hydrate (10).
1,1'-Dimethyl-4,4'-dodecane-1,12-diylbis[quinolinium]Diiodide
4,4'-Decane-1,10-diylbis[quinoline]
1,1'-Dimethyl-4,4'-decane-1,10-diylbis[quinolinium]Diiodide
1,10-Bis[N-(1-benzylquinolinium-4-yl)amino]decane Dibromide
1,10-Bis[N-(1-benzyl-2-methylquinolinium-4-yl)amino]-decane Bis(trifluoroacetate)
1,12-Bis[N-(1-benzyl-2-methylquinolinium-4-yl)amino]-dodecane Bis(trifluoroacetate)
1-[N-(1-Benzyl-2-methylquinolinium-4-yl)amino]-10-[N-(2-methylquinolinium-4-yl)amino]decane Bis(trifluoroacetate)
1-[N-(1-Benzyl-2-methylquinolinium-4-yl)amino]-12-(N-(2-methylquinolinium-4-yl)amino]dodecane Bis(trifluoroacetate)-3,5-Dimethoxybenzyl iodide
1,10-Bis[N-[1-(3,5-dimethoxybenzyl)-2-methylquinolinium-4-yl]amino]decane Bis(trifluoroacetate)
1-[N-[1-(3,5-Dimethoxybenzyl)-2-methylquinolinium-4-yl]amino]-10-[N'-(2-methylquinolinium-4-yl)amino]decane Bis(trifluoroacetate)
1,1'-(3-Iodopropylidene)bis[benzene]
1,10-Bis[N-[1-(3,3-diphenylprop-1-yl)-2-methylquinolinium-4-yl]amino]decane Bis(trifluoroacetate)
4,7-Dichloro-1-methylquinolinium Iodide
1,10-Bis[N-(7-chloro-1-methylquinolinium-4-yl)amino]-decane Diiodide Dihydrate.

Dequalinium and its salts are commercially available, for example from (Sigma Aldrich). Methods of making suitable analogues are described in WO 97/48705, Galanakis et al. (1995) *J. Med. Chem.* 38: 595-606, Galanakis et al (1995) *J. Med. Chem.* 38: 3536-3546 and Galanakis et al (1996) *J. Med. Chem.* 39: 3592-3595, Abeywickrama et al. (2006) *Bioorganic Medicinal Chem.* 14: 7796-7803, Qin et al. (2000) *J. Med. Chem.* 43: 1413-1417, Campos Rosa et al (1996) *J. Med. Chem.* 39: 4247-4254, the contents of which are incorporated herein by reference. In particular, the synthesis of Compound 7 is described in Galanakis et al. (1995) supra and the synthesis of Compound 7_12 may be derived therefrom.

The compounds of formula (IV) and (V) may be prepared by methods analogous to the known methods for preparing dequalinium, as described and referenced above.

For example, compounds of the formulae (IV) and (V) can be prepared by the reaction of a quinoline compound of the formula (VI):

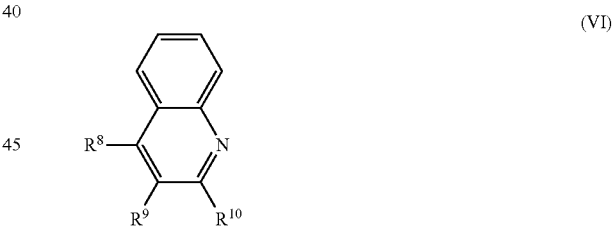

with a compound of the formula I—$(CH_2)_r$—I. The reaction is typically carried out at an elevated temperature, for example in the range 120° C. to 160° C., e.g. at around 150° C.

Quinoline compounds of the formula (VI) are commercially available or can be made by standard methods well known to the skilled person or methods analogous thereto, see for example *Advanced Organic Chemistry* by Jerry March, 4th Edition, John Wiley & Sons, 1992, *Organic Syntheses*, Volumes 1-8, John Wiley, edited by Jeremiah P. Freeman (ISBN: 0-471-31192-8), 1995, *Fiesers' Reagents for Organic Synthesis*, Volumes 1-17, John Wiley, edited by Mary Fieser (ISBN: 0-471-58283-2), and Handbook of Heterocyclic Chemistry, A. R. Katritzky et al, 3rd Edition, Elsevier, 2010.

Compounds of the formula (VI) wherein $R^8$ is amino and $R^9$ and $R^{10}$ link together to form an alkylene chain $(CH_2)_w$ can be prepared by means of the following reaction sequence:

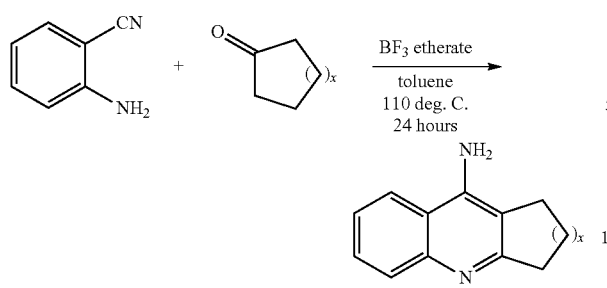

The amino group may then be converted into other functional groups by standard methods, for example by Diazotisation followed by a Sandmeyer reaction.

The nucleic acid sequence may be an oligonucleotide sequence or a polynucleotide sequence. An oligonucleotide sequence is generally recognised as a linear sequence of up to 20 nucleotides joined by phosphodiester bonds, while a polynucleotide sequence typically has more than 20 nucleotides and maybe single or double stranded with varying amounts of internal folding. The backbone may also be modified to incorporate synthetic chemistries known either to reduce the charge of the molecule or increase its stability in biological fluids. Examples of these include peptide nucleic acids (PNA), linked nucleic acids (LNA), morpholino oligonucleotides and phosphorothioate nucleotides and combinations of these.

In one embodiment, the nucleic acid sequence comprises the sequence of a native cellular binding site for a transcription factor. Such a sequence is referred to as a transcription factor decoy (TFD). Preferably the decoy comprises the sequence of a bacterial Sig binding site. Alternatively, the decoy comprises the sequence of a bacterial Fur binding site.

Examples of suitable TFD sequences are provided in SEQ ID NOs: 11, 12, 13, 32, 33, 39, 40, 41, 42, 43 and 44.

TFDs are effective at nanomolar concentrations and have been effective at preventing growth of bacteria in vitro and in vivo at concentrations as low as 1 nM, although it is anticipated that against certain bacteria and in more complex settings, such as in a patient higher concentrations may be needed. Hence, a preferred range would therefore be between about 10 to 100 nM, and up to around 1 µM. It will be appreciated that the range encompasses concentrations in between about 10 nM and 1 µM, such as 20 nM, 20 nM, 40 nM, 50 nM, 60 nM, 70 nM, 80 nM, 90 nM, 150 nM, 200 nM, 500 nM, 750 nM, and intermediates thereof, for example 27.2 nM.

Where the delivery moiety is a compound of any of formulae (I) to (V) such as dequalinium or an analogue thereof, complexes are formed between the nucleic acid and the compound (e.g. dequalinium or an analogue thereof) using different ratios of both. The ratio is commonly referred to as the N/P ratio (for example see Zhao et al. (2007) *Biomacromolecules* 8: 3493-3502), which defines the number of positively Nitrogen atoms in the delivery molecule per negatively charged Phosphate atom in the nucleic acid, or per nucleotide when no phosphate atoms are present. Typically complexes are formed between dequalinium (or its analogues) and TFDs at N/P ratios between 0.1 and 1 (which is sufficient to achieve charge neutralisation). It will be appreciated that the present invention encompasses ratios in between 0.1 and 1, such as 0.2, 0.3, 0.4, 0.5, 0.6, 0.7, 0.8, 0.9 and intermediates thereof, e.g. 0.23.

Complexes capable of transfecting bacteria in vitro are well tolerated in animal studies. Furthermore, the components of such complexes may be used at concentrations below their known Maximum Tolerated Dose (MTD). Maximum Tolerated Dose (MTD) is the highest daily dose that does not cause overt toxicity. MIC can be estimated by animal studies as the amount of compound that, when administered to a group of test animals, has no measurable affect on long term survivability. For example, administering a complex containing 1 µM of a 100 nucleotide TFD with an N/P ratio of 1 would give a dose of approximately 3 mg/kg dequalinium analogue. It will be appreciated that this dose of dequalinium analogue is substantially below the MTD of dequalinium. The analogues of dequlanium, such as Compound 7, show less in vitro toxicity than dequalinium (Weissig et al. (2006) *J. Liposome Res.* 16: 249-264). Because dequalinium has an MTD of 15 mg/kg in mice (Gamboa-Vujicic et al. (2006) *J. Pharm. Sci.* 82: 231-235) it is predicted that the complexes should be well tolerated. It is within the reasonable skill and knowledge of the skilled person to calculate and prepare suitable concentrations.

In an alternative embodiment, the antibacterial complex comprises a nucleic acid sequence and an antibacterial peptide. The term antibacterial peptide includes and encompasses antimicrobial peptides, cell penetrating peptides, non-ribosomally synthesised peptides and glycopeptides.

Antimicrobial peptides (AMPs; also called host defense peptides) are ancient and natural antimicrobials that are diverse and widespread. They are an evolutionarily conserved component of the innate immune response and are found among all classes of life. Fundamental differences exist between prokaryotic and eukaryotic cells that may represent targets for antimicrobial peptides. These peptides are potent, broad spectrum antibiotics which demonstrate potential as novel therapeutic agents. Antimicrobial peptides have been demonstrated to kill Gram-negative and Gram-positive bacteria (including strains that are resistant to conventional antibiotics), mycobacteria (including *Mycobacterium tuberculosis*), enveloped viruses and fungi. Unlike the majority of conventional antibiotics, it appears that antimicrobial peptides may also have the ability to enhance immunity by functioning as immunomodulators.

Antimicrobial peptides are generally between 12 and 50 amino acids. These peptides include two or more positively charged residues provided by arginine, lysine or, in acidic environments, histidine, and a large proportion (generally >50%) of hydrophobic residues. The secondary structures of these molecules follow four themes, including i) α-helical, ii) β-stranded due to the presence of two or more disulfide bonds, iii) β-hairpin or loop due to the presence of a single disulfide bond and/or cyclisation of the peptide chain, and iv) extended. Many of these peptides are unstructured in free solution and fold into their final configuration upon partitioning into biological membranes. The peptides contain hydrophilic amino acid residues aligned along one side and hydrophobic amino acid residues aligned along the opposite side of a helical molecule. This amphipathicity of the antimicrobial peptides allows the peptides to partition into the membrane lipid bilayer. These peptides have a variety of antimicrobial activities ranging from membrane permeabilisation to action on a range of cytoplasmic targets.

The modes of action by which antimicrobial peptides kill bacteria is varied and includes disrupting membranes, interfering with metabolism, and targeting cytoplasmic components. The initial contact between the peptide and the target organism would be electrostatic, as most bacterial surfaces are anionic. Their amino acid composition, amphipathicity, cationic charge and size allow them to attach to and insert into membrane bilayers to form pores by 'barrel-stave', 'carpet' or 'toroidal-pore' mechanisms. Once the cell has been penetrated, the peptides bind to intracellular molecules which are crucial to cell living, thereby inhibiting cell wall synthesis, altering the cytoplasmic membrane, activating autolysin, inhibiting DNA, RNA, and protein synthesis, and inhibiting certain enzymes. However, in many cases, the exact mechanism of killing is not known. In contrast to many conventional antibiotics, these peptides appear to be bacteriocidal (bacteria killer) instead of bacteriostatic (bacteria growth inhibitor).

In the competition of bacterial cells and host cells with the antimicrobial peptides, antimicrobial peptides will preferentially interact with the bacterial cell to the mammalian cells, which enables them to kill microorganisms without being significantly toxic to mammalian cells. Since the surface of the bacterial membranes is more negatively charged than mammalian cells, antimicrobial peptides will show different affinities towards the bacterial membranes and mammalian cell membranes.

It is well known that cholesterol is normally widely distributed in the mammalian cell membranes as a membrane stabilizing agents but is absent in bacterial cell membranes. The presence of these cholesterols will also generally reduce the activities of the antimicrobial peptides, due either to stabilisation of the lipid bilayer or to interactions between cholesterol and the peptide. Thus, the cholesterol in mammalian cells will protect the cells from attack by the antimicrobial peptides.

In addition, the transmembrane potential is well-known to affect peptide-lipid interactions. A negative transmembrane potential exists between the outer leaflet to the inner leaflet of a cell membrane. This inside-negative transmembrane potential facilitates membrane permeabilisation probably by facilitating the insertion of positively charged peptides into membranes. By comparison, the transmembrane potential of bacterial cells is more negative than that of normal mammalian cells, so bacterial membrane will be prone to be attacked by the positively charged antimicrobial peptides.

As discussed above, AMPs are a unique and diverse group of molecules, which are divided into sub-groups on the basis of their amino acid composition and structure. A database of many of the known AMPs can be found at http://www.bbc-m.units.it/~tossi/pag1.htm. Other groups of peptides with anti-infective properties include the non-ribosomal peptides, examples of which include gramicidin, and as a sub-group those with glycopeptides antibiotics, where peptides (which are commonly cyclic) are glycosylated. Examples of these include Polymyxin.

The present inventors have made a functional classification of all of these peptides, which are termed Anti-Bacterial Peptides (ABPs) herein, to distinguish them from AMPs, based on the mechanism of bacterial killing, and include peptides derived from other classes of antibacterials such as cell-penetrating peptides, non-ribosomally synthesised peptides and glycopeptides. It will be appreciated that the invention encompasses naturally occurring and non-naturally occurring, synthetic peptides.

Class I.

ABPs that are membrane active (Polymyxin, gramicidin) and affect entry by causing sufficient damage to punch holes in the outer membrane and allow extrusions (or 'blebs') of the bacterial inner membrane to form, through which large molecules can pass. Several of these peptides are used in the clinic but there are concerns about toxicity as they damage eukaryotic membranes as well.

The rate of resistance against antibacterial peptides is remarkably low and these peptides are widespread in nature. As this class is predominantly cationic, resistance mechanisms would take the form of changes to charge density on the outer membrane of bacteria, and such changes have been seen in the lab. Hence, the relative low incidence of resistance may reflect the fact that the ABPs are not that effective, rather than being difficult to resist.

Class II.

This is a much smaller class. These ABPs do not damage the membrane but instead have intracellular targets. Thus, the peptides must translocate through the bacterial membranes to reach their targets. As a result, they are markedly less toxic than Class I ABPs as they do not damage eukaryotic membranes causing haemolysis etc. Although they are cationic, their ability to cross membranes is not expected to be solely predicated on their charge but other broader structural properties, which largely remain undefined. As consequence, resistance mechanisms are thought less likely to occur as such mechanisms would need to alter the hydrophobic nature of the bacterial membranes themselves.

An example of an ABP that is capable of translocation is Buforin and a truncated form Buforin II (BF2). This peptide shows (weak) broad spectrum activity against pathogenic bacteria (Park et al. (2000) *Proc. Natl. Acad. Sci USA* 97: 8245-8250). It has been used to translocate eukaryotic membranes and even to deliver a 28 kDa peptide (GFP) to human cell lines (Takeshima et al. (2003) *J. Biol. Chem.* 278: 1310-1315), although this was via endocytosis and probably due to the cationic nature of the peptide.

The ABP may be a naturally occurring peptide, such as Gramicidin, or Buforin Alternatively, the ABP may be a peptidomimetic or a synthetic variant of a naturally occurring peptide, such as Buforin II or Polymyxin nonapeptide.

Examples of antimicrobial peptides with the ability to permeabilise biological membranes are provided in Papagianni et al ((2003) *Biotechnol. Adv.* 21: 465-499) and include defensins, pleuricidins, magainins, dermaseptins, apidaecins, cecropins, microcins and pediocins.

Examples of antibacterial peptides with the ability to permeabilise biological membranes are provided in Varra et al ((1992) *Microbiol. Rev.* 56: 395-411) and include the lantibiotics, glycopeptide antibiotics, cationic polypeptides such as polylysine and polyarginine.

Types and characteristics of ABPs are summarised in Table 1:

| Type | Characteristic | ABPs |
|---|---|---|
| Anionic peptides | rich in glutamic and aspartic acids | Maximin H5 from amphibians, Dermcidin from humans |
| Linear cationic α-helical peptides | lack in cysteine | Cecropins, andropin, moricin, ceratotoxin and melittin from insects, Magainin, dermaseptin, bombinin, brevinin-1, esculentins and buforin II from amphibians, CAP18 from rabbits, LL37 from humans |
| Catioinic peptide enriched for specific amino acid | rich in proline, arginine phenylalanine, glycine tryptophan | abaecin, apidaecins from honeybees, prophenin from pigs, indolicidin from cattle. |

| Type | Characteristic | ABPs |
|---|---|---|
| Anionic and cationic peptides that contain cysteine and form disulfide bonds | contain 1~3 disulphide bond | 1 bond:brevinins, 2 bonds:protegrin from pig, tachyplesins from horsehoe crabs, 3 bonds:defensins from humans more than 3:drosomycin in fruit flies |
| Anionic and cationic peptide fragments of larger proteins | Generated by peptidic cleavage | Cascocidin I from human casein, lactoferricin from lactoferrin, antimicrobial domains from human haemoglobin or lysozyme |

The ABP may be linked to the nucleic acid by electrostatic or covalent linkages. In particular, where the mechanism of killing of the ABP is via intracellular targeting, rather than membrane permeabilisation, the complex ideally includes covalent linkage, such as a suitable linker or cross-linker between the nucleic acid sequence and the ABP. An example of a suitable linker is one that couples a carboxyl group to a primary amine. For example, a suitable linker may be EDC (1-ethyl-3-[3-dimethylaminopropyl]carbodiimide hydrochloride).

EDC is known for its use as a carboxyl activating agent for the coupling of primary amines to yield amide bonds and a common use for this carbodiimide is protein cross-linking to nucleic acids.

Although ABPs have antimicrobial activity on their own, it has been found that such peptides act synergistically when in combination with TFDs to prevent bacterial growth. Some ABPs have a bacteriostatic effect and others rapidly kill on contact. It has been found that sub-lethal concentrations of the peptides allow entry of TFDs. The peptides stress the bacteria making them more vulnerable to TFDs, which then block stress causing growth stasis or cell death.

The complexes are prepared so that the ABPs are at a concentration that is typically 5-10 fold less than their Minimum Inhibitory Concentration (MIC). The MIC of a compound is the minimum concentration of that compound to prevent visible growth of the bacteria. Typically the MIC is determined by a dilution method where inoculated cultures of bacteria are incubated overnight with a series of concentrations of the compound and the one that prevents growth is taken as the MIC. It is within the reasonable skill and knowledge of the skilled person to calculate and prepare suitable concentrations.

In a yet further embodiment, the antibacterial complex of the present invention comprises a) a nucleic acid sequence, b) a quaternary amine compound or bis-aminoalkane, or unsaturated derivative thereof, wherein the amino component of the aminoalkane is an amino group forming part of a heterocyclic ring, and c) an antibacterial peptide.

Expressed in another way, the antibacterial complex of the present invention comprises a) a nucleic acid sequence, b) a quarternary derivative of quinoline or acridine, and c) an antibacterial peptide.

In a particularly preferred embodiment, the antibacterial complex comprises a) a transcription factor decoy, b) a dequalinium analogue and optionally, c) an antimicrobial peptide.

In a yet further aspect, the present invention residues in use of the complexes of the invention in a suitable formulation for the treatment of one or more bacterial infections.

In particular, the invention provides a method for treating bacterial infection in a subject comprising administering a nucleic acid sequence formulated as described herein. The subject may be a human or animal. The invention also provides a nucleic acid sequence formulated as described herein for use in medicine, e.g. for use in treating or preventing bacterial infection in a subject, and the use of the nucleic acid sequence formulated as described herein for the manufacture of a medicament for treating bacterial infection.

The invention further relates to a pharmaceutical composition or medicament comprising a nucleic acid sequence, a nucleic acid sequence, at least one delivery moiety, wherein the delivery moiety is selected from quaternary amine compounds; bis-aminoalkanes and unsaturated derivatives thereof, wherein the amino component of the aminoalkane is an amino group forming part of a heterocyclic ring; and an antibacterial peptide and a physiologically acceptable carrier or excipient. The composition may additionally comprise one or more antibiotic or other antibacterial compound or composition.

The number of nucleic acid sequences needed to show a predictable effect on expression of a targeted gene and have a bacteriostatic or bacteriocidal effect can be as little as circa 5000 molecules per cell. It has been found that as many as 1,000,000 bacterial cells are efficiently killed with as little as 1 nM of TFD (WO/2010/038083), suggesting that it is sufficient to have a transfection efficiency of less than 0.001% to achieve killing. In comparison with other nucleic acid-based strategies to tackle bacterial infections, such as antisense, this number of molecules needed to kill the cell is 100 to 1000-fold less. This partly reflects that although both antisense approaches and TFDs act to inhibit genes, TFDs act at an early step to prevent transcription whilst antisense, in the most common iteration, sterically blocks the products of transcription: many thousands of mRNAs molecules. Secondly, the TFDs have been designed to target essential genes that are positively induced, so need to be switched on for survival, and positively regulated (the transcription factor drives its own production). In vitro, this latter characteristic means that relatively few copies of the transcription factor are likely present when the gene is uninduced and so a small number of TFDs can block induction.

It may be that, in a therapeutic situation, there are more transcription factors per cell, due to natural variety amongst the bacterial population or the gene being already induced. In this situation it is expected that more TFDs will be needed to see a therapeutic effect and estimate that increasing the dose by a factor of 100 (to 100 nM) or improving the transfection efficiency (by two orders of magnitude) will be sufficient to see a beneficial effect. Transfection may be quantified using fluorescence microscopy (Zhang et al. (1996) *J. Mol. Neurosci.* 7: 13-28).

Pharmaceutical compositions according to the present invention, and for use in accordance with the present invention, may comprise as, or in addition to active ingredient, a pharmaceutically acceptable excipient or diluent any suitable binder, lubricant, suspending agent, coating agent, solubilising agent or other materials well known to those skilled in the art. Such materials should be non-toxic and should not interfere with the efficacy of the active ingredient. Acceptable carriers or diluents for therapeutic use are well known in the pharmaceutical art, and are described, for example, in Remington' Pharmaceutical Sciences, Mack Publishing Co. (A. R. Gennaro edit. 1985). The precise nature of the carrier or other material will depend on the route of administration, which may be oral, or by injection, e.g. cutaneous, subcutaneous or intravenous.

The active ingredient is defined as a nucleic acid sequence, such as a TFD, complexed (or formulated) with a delivery moiety, the delivery moiety being the delivery moiety is selected from quaternary amine compounds; bis-aminoalkanes and unsaturated derivatives thereof, wherein the amino component of the aminoalkane is an amino group forming part of a heterocyclic ring; and an antibacterial peptide. In the complex/formulation, the quaternary amine compound, bis-aminoalkane or unsaturated derivative thereof, such as dequalinium or its analogue, is in the form of a bolasome. The term 'bolasome' is used in this specification to describe vesicles of the derivative after the compound has been subjected to sonication (see Weissig and Torchilin (2001) *Adv. Drug Delivery Rev.* 49: 127-149).

A variety of methods may be used to deliver the antibacterial complex of the present invention to the site of bacterial infection. Methods for in vivo and/or in vitro delivery include, but are not limited to, buccal or oral delivery, intravenous delivery, direct injection into the infection or indirect injection (e.g. subcutaneous, intraperitoneal, intramuscular, or other injection methods), topical application, direct exposure in aqueous or media solution, transfection (e.g. calcium phosphate, electroporation, DEAE-dextran based, and lipid mediated), transgenic expression (e.g. a decoy expression system delivered by microinjection, embryonic stem cell generation, or retroviral transfer), or any of the other commonly used nucleic acid delivery systems known in the art. Administration may be in combination with a suitable dose of antibiotic, with the antibiotic(s) being administered at the same time as the nucleic acid sequence, or separately.

Pharmaceutical compositions for oral administration may be in tablet, capsule, powder or liquid form. A tablet may comprise a solid carrier such as gelatine or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, tonicity and stability. Those of relevant skill in the art are well able to prepare suitable solutions using, for example, isotonic vehicles such as sodium chloride, Ringer's injection, lactated Ringer's injection, preservatives, stabilisers, buffers, antioxidants and/or other additives may be included, as required.

For some applications, pharmaceutical formulation may not be required. For example, the antibacterial complex of the invention may be tolerated as a pharmaceutical in its own right, without the need for excipients and/or carriers.

Alternatively, the antibacterial complex may be suitable for use as an antibacterial disinfectant and so may be required in a suitable aqueous format. In which instance, the complex may further comprise aqueous and organic solvents and their combinations.

The antibacterial complex of the invention may be used to treat a variety of bacterial infections wherever they occur within the human body. Five general areas of bacterial infection can be described.

Respiratory tract infections are amongst the commonest, the upper respiratory tract infections including the ears, throat, and nasal sinuses that can be treated with tropical applications or aerosol preparations. Lower tract infections include pneumonia (which is caused by a range of bacterial pathogens, bronchitis and infective complications of cystic fibrosis.

A common problem in both community and hospital practice is urinary tract infections, where the urine becomes infected and antibacterials need to enter the bladder, prostrate, ureter and kidneys.

The gut is vulnerable to infections, where bacteria cause disease by either by mucosal invasion or toxin production, an example of which includes cholera epidemics, and when used antibiotics are either ingested or administered intravenously.

Skin and soft tissue infections, which can be treated by topical applications, are common following traumatic injury or burns, which allow colonisation and ingression of microorganisms resulting in infections that are both localised or have spread rapidly through tissues. Microbes responsible for skin infections often arise from normal skin flora, such as *Streptococcus pyogenes* causing superficial skin infections (impetigo), cellulitis (more deep-seated infection that can spread to the blood) and necrotising fasciitis, a rapidly progressive infection that is often life-threatening.

Finally infections of the central nervous system, such as bacterial meningitis, are perhaps the most challenging to treat as therapies must penetrate the blood-brain barrier, as too have the pathogenic bacteria.

The antibacterial complex of the present invention may be used in combination with one or more antibiotics to which the nucleic acid sequence makes the bacterial cell more sensitive, and/or with another antibacterial agent. Suitable antibiotics are described in co-pending applications WO 2009/044154 and WO 2010/038083. It will be appreciated that the lists provided therein may not be exhaustive. The present invention encompasses any suitable antibiotic or antibacterial compounds or compositions.

The antibiotic or antibacterial compound may be administered simultaneously with, or before or after the antibacterial complex of the invention. The antibiotic/antibacterial compound and antibacterial complex may be administered in the same or in separate compositions. Thus the invention includes combination therapies in which an antibacterial complex as identified, and/or as described, herein is administered to a subject in combination with one or more antibiotics or other antibacterial therapies. The composition may additionally comprise one or more antibiotic or other antibacterial compounds or compositions.

Suitable TFDs encompassed by the invention and/or their targets are listed below. The sequences provided herein illustrate single strands of the binding sites. However, it will be appreciated that in nature and in the TFDs of the present invention, the sequences will be double stranded. The complementary strands to the sequences listed herein are clearly and easily derivable, for example from Molecular Cloning: A Laboratory Manual (3$^{rd}$ Edition), 2001 by Joseph Sambrook and David Russell.

WhiB7

The native WhiB7 binding site in *M. smegmatis* str MC2 155 comprises:

(SEQ ID NO: 1)
5'- CACCAGCCGA AAAGGCCACG GACCCGCAGT CACCCGGATC CGTGGCCATT

TTTGTCGGAC CCCCCGAGAA ATCTGGTCGC AGGATCCATC AGCTCAGACA GATCAC- 3'

WhiB7 TFD:

```
                                              (SEQ ID NO: 2)
  5' TGG CCA CGG ATC CGG GTG ACT GCG GGT CCG TGG

CCT 3'
```

FadR

The native FadR binding site in *E. coli* K12 comprises the sequence:

```
                                              (SEQ ID NO: 3)
  5' AGTAAGTTTC GAATGCACAA TAGCGTACAC TTGTACGCCG

AACAAGTCCG ATCAGCCATT TAA-3'
```

One example of a FadR TFD sequence comprises

```
                                              (SEQ ID NO: 4)
  5' TTT ATT CCG AAC TGA TCG GAC TTG TTC AGC GTA CAC

GTG TTA GCT ATC CTG CGT GCT TCA 3'
```

YycG/YycF

The native binding sites for YycF and YycG in *S. aureus* (in the LytM and Ssa promoters) comprise:

```
  YycF_LytM
                                              (SEQ ID NO: 5)
  5'-GCTATTTTGTAATGACAATGTAATGAGTTTAGTAAAAA-3'

YycF_SsaA
                                              (SEQ ID NO: 6)
  5'-ATTACAAATTTGTAACAGACTTATTTTA-3'
```

Examples of a YycG/YycF TFD sequence include:

```
  LytM TFD
                                              (SEQ ID NO: 7)
  5' GCT ATT TTG TAA TGA CAA TGT AAT GAG TTT AGT AAA

AA 3'

SsaA TFD
                                              (SEQ ID NO: 8)
  5' ATT ACA AAT TTG TAA CAG ACT TAT TTT A 3'
```

Sigma 54 or Sig$^B$

The native binding sites in *S. aureus* and *K. pneumoniae* comprise:

```
  SA_sig:
                                              (SEQ ID NO: 9)
  5'-TTATTATATA CCCATCGAAA TAATTTCTAA TCTTC-3'

KP_sig:
                                              (SEQ ID NO: 10)
  5'-CCGATAAGGG CGCACGGTTT GCATGGTTAT-3'
```

Fur

Consensus sequences for Fur binding in *S. aureus* and *E. coli* comprise:

```
                                              (SEQ ID NO: 11)
  SA_fur: 5'-ACT ACA AGT ACT ATT AGT AAT AGT TAA CCC

TT-3'.
```

Consensus sequence ('Fur BOX') as described in Horsburgh, *J. Bacteriology* (2001) 183:468.

EC_fur: 5'-GATAATGATAATCATTATC-3' (SEQ ID NO: 12). Consensus sequence as described in de Lorenzo, *J. Mol. Biol.* (1998) 283:537.

A native binding sequence in *H. pylori* comprises:

```
                                              (SEQ ID NO: 13)
  HP_fur: 5'-GTT GTC CCA TAA TTA TAG CAT AAA TGA TAA

TGA AAA AGT AAA-3'
```

TcdR

A consensus binding site in *C. difficile* comprises:

```
                                              (SEQ ID NO: 14)
  5'-AAG TTT ACA AAA TTA TAT TAG AAT AAC TTT TTT A

TT-3'.
```

Consensus sequence (TcdR, where −35 and −10 boxes are underlined) as described in Dupuy, *Mol. Micro.* (2006) 55:1196.

Vfr

A consensus and two native binding sites in *P. aeruginosa* are:

PA_Vfr: 5'-AAA TGT GAT CTA GAT CAC ATT T-3' (SEQ ID NO: 15). Consensus sequence as described in Kanack, *Microbiol.* (2006) 55:1196.

```
                                              (SEQ ID NO: 16)
  PA_ToxA: 5'-CACTCTGCAA TCCAGTTCAT AAATCC-3'

(SEQ ID NO: 17)
  PA RegA: 5'-GTAACAGCGGAACCACTGCACAG-3'
```

NtrC

A native binding site in *K. pneumoniae* comprises:

```
                                              (SEQ ID NO: 18)
  5'-GCTTTGCACTACCGCGGCCCATCCCTGCCCCAAAACGATCGCT-3'
```

ArsR

Examples of a native binding sequence comprise:

```
  HP_AmiE:
                                              (SEQ ID NO: 19)
  5'-ATAATCATAA TGATTAAAGT TTTCATATTC ATTATAAATC

CGTTTACACA ATTATT-3'

HP_RocF:
                                              (SEQ ID NO: 20)
  5'-GAAATTGTTC TATTTATTAT CCATTTGCTT ATTAATAATT

GGTTGTTAAT TTTGGTTTAG A-3'
```

Glycopeptide-Resistant Consensus Sequence (GISA)

An example of the consensus sequence, found in the promoter of tcaA, a known positive regulator of virulence (Maki, *Antimicrobial Agents Chemother.* (2004) 48:1953) may be used in an antibacterial complex of the invention, for example:

```
                                             (SEQ ID NO: 21)
    SA_TcaA: 5'-TGAACACCTTCTTTTA-3'
```

AqrA

Examples of a sequences for motifs found in genes to be positively regulated by Agr, a regulator associated with virulence (Dunman, *J. Bacteriol.* (2001) 183:7341) are:

```
                                             (SEQ ID NO: 22)
    SA_Agr_2093: 5'-AGA AAG ACA AAC AGG AGT AA-3'

(SEQ ID NO: 23)
    SA_Agr_1269: 5'-GAA GAA ACA AAA AGC AGC AT-3'
```

Suitable primer sequences for a *S. aureus* Sig TFD are:

```
SAsigB FOR:
                                             (SEQ ID NO: 24)
GAA GAT TAG AAA TTA TTT CGA T GGG TAT ATA ATA A;
and SASigB REV:
                                             (SEQ ID NO: 25)
TAT TAT ATA CCC ATC GAA ATA ATT TCT AAT CTT C A.
```

Suitable primer sequences for a *S. aureus* Fhu TFD are:

```
SAfhu FOR:
                                             (SEQ ID NO: 26)
ACT ACA AGT ACT ATT AGT AAT AGT TAA CCC TA;
and SAfhu REV:
                                             (SEQ ID NO: 27)
AGG GTT AAC TAT TAC TAA TAG TAC TTG TAG TA
```

Suitable primer sequences for an *S. aureus* SsaA TFD are:

```
                                             SEQ ID NO: 28
SsaA FOR: ATT ACA AAT TTG TAA CAG ACT TAT TTT A);
and SEQ ID NO: 29
SsaA REV: AAA ATA AGT CTG TTA CAA ATT TGT AAT A
```

To form a Sig dumbbell TFD (referred to as SA3 TFD), the following phosphorylated oligonucleotides may be synthesised:

```
SigDB_SA3:
                                             (SEQ ID NO: 30)
CTTGG TTTTT CCAAG GAA GAT TAG AAA TTA TTT CGA T

GGG TAT ATA ATA;
and

SigDB_SA3:
                                             (SEQ ID NO: 31)
P-CCG TCT TTT TGA CGG TAT TAT ATA CCC ATC GAA ATA

ATT TCT AAT CTT C
```

The sequences of the pairs of oligonucleotides used to form a WalR_TFD are:

```
WalR1:
                                             (SEQ ID NO: 32)
5'-P-CTT GGT TTT TCC AAG TAA TGA ATG AGT TTA AAG

CCC ATG TAA AAG GGG TAT CAG TAC-3';
and

WalR2:
                                             (SEQ ID NO: 33)
5'-P-CCC TCT TTT TGA GGG GTA CTG ATA CCC CTT TTA

CAT GGG CTT TAA ACT CAT TCA TTA-3'.
```

Other suitable primers for TFDs include:

```
fabBf:
                                             (SEQ ID NO: 34)
5'-tct tta aat ggc tga tcg gac ttg-3';
and fabBr
                                             (SEQ ID NO: 35)
5'-agt aag ttt cga atg cac aat agc gta-3'.

Ks54f:
                                             (SEQ ID NO: 36)
P-CCG ATA AGG GCG CAC GGT TTG CAT GGT TAT A;
and Ks54r:
                                             (SEQ ID NO: 37)
P-ATA ACC ATG CAA ACC GTG CGC CCT TAT CGG A.
```

A consensus sequence for a WalR_TFD may be TGT WAW NNN NNT GTA AW (SEQ ID NO: 38) where: W is A or T.

A consensus sequence for a SigB TFD may be GKT TWA NNN NNN NNN NNN NNK GGT AW (SEQ ID NO: 39) where: K is G or T; W is A or T.

An example of a KP sig TFD sequence is TGG CAC AGA TTT CGC T (SEQ ID NO: 40)

A consensus sequence for a KP_Sig TFD may be TGG NNN NNN WTT TGC W (SEQ ID NO: 41) where W is A or T.

Such TFDs may be prepared and tested as described in co-pending applications WO 2009/044154 and WO 2009/044154.

The Invention will now be Further Described by Way of Non-Limiting Examples and Figures:

FIG. 1. Chemical structure of Dequalinium.

FIG. 2. Chemical structure of 10,10'-(decane-1,10-diyl)bis (9-amino-1,2,3,4-tetrahydroacridinium)dichloride.

Figure 3:
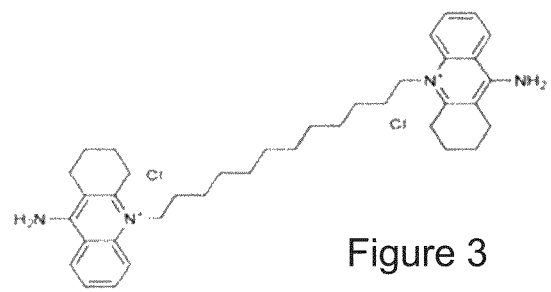

FIG. 3. Chemical structure of 10,10'-(dodecane-1,12-diyl) bis(9-amino-1,2,3,4-tetrahydroacridinium)dichloride.

Figure 4:
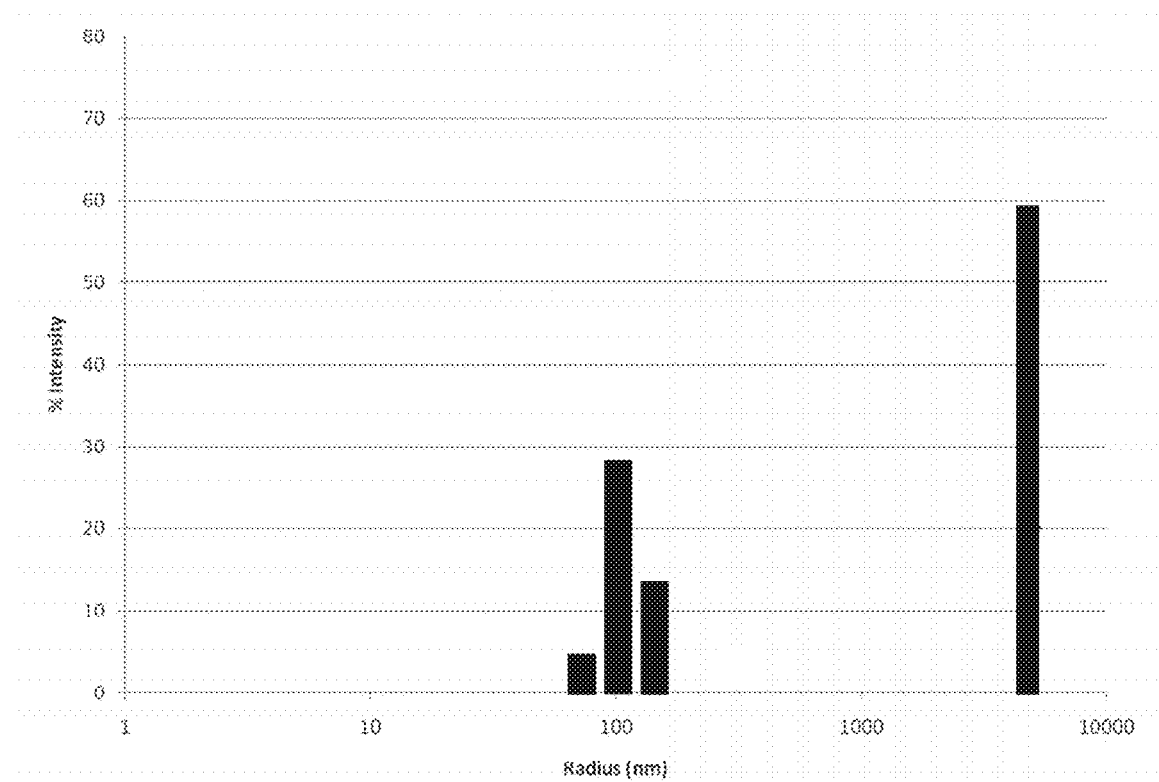

FIG. 4. Size distribution of 100 μM sC7 bolasomes as measured by dynamic light scattering.

Figure 5:
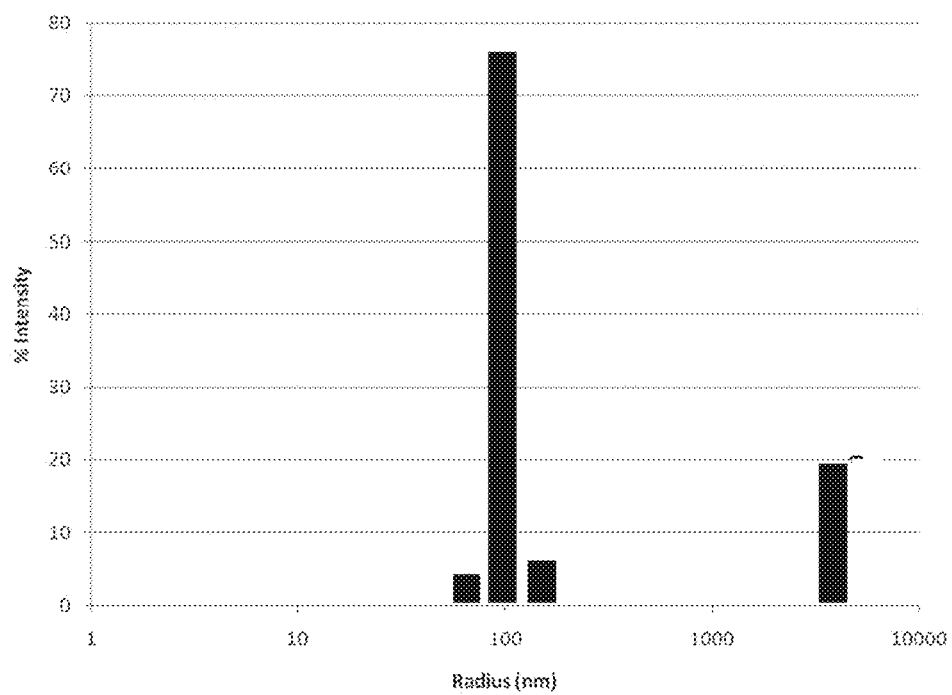

FIG. 5. Size distribution of 100 μM sC7_12 bolasomes as measured by dynamic light scattering.

Figure 6:
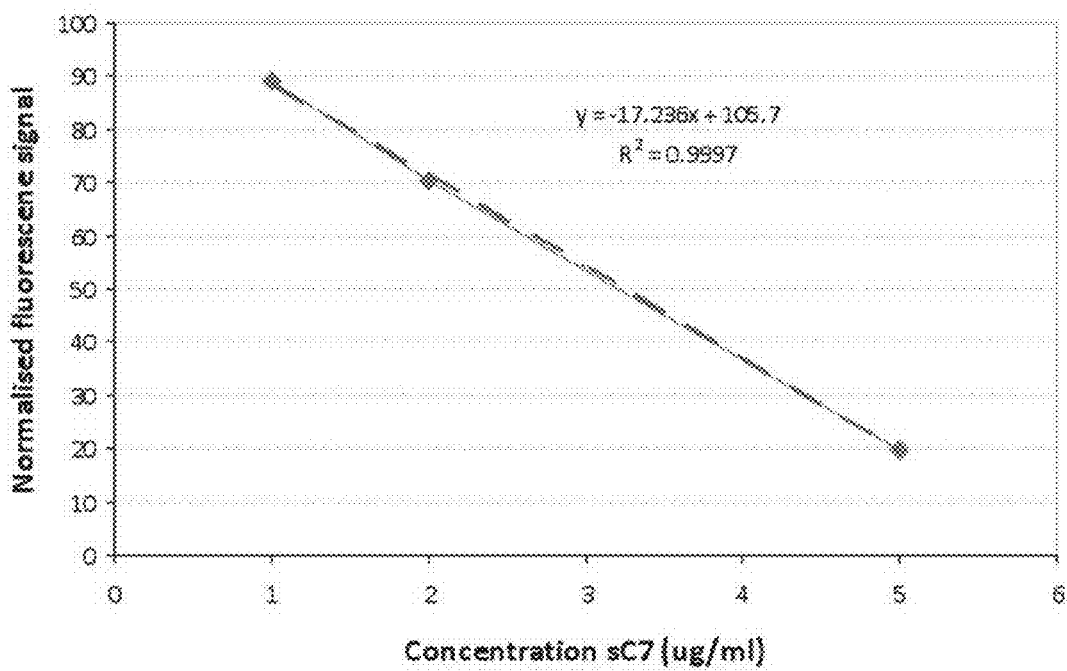

FIG. 6. SYBR Green-DNA binding assay to measure binding of Compound 7 bolasomes to TFDs.

Figure 7:
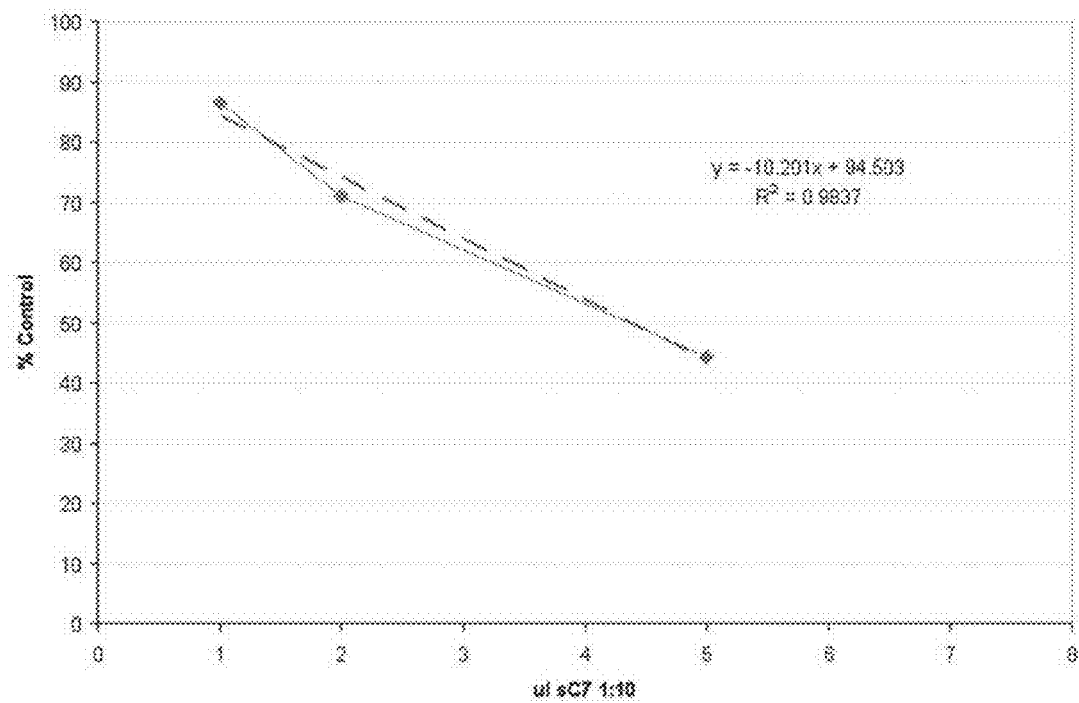

FIG. 7. SYBR Green-DNA binding assay to measure binding of Compound 7_12 bolasomes to TFDs.

Figure 8:
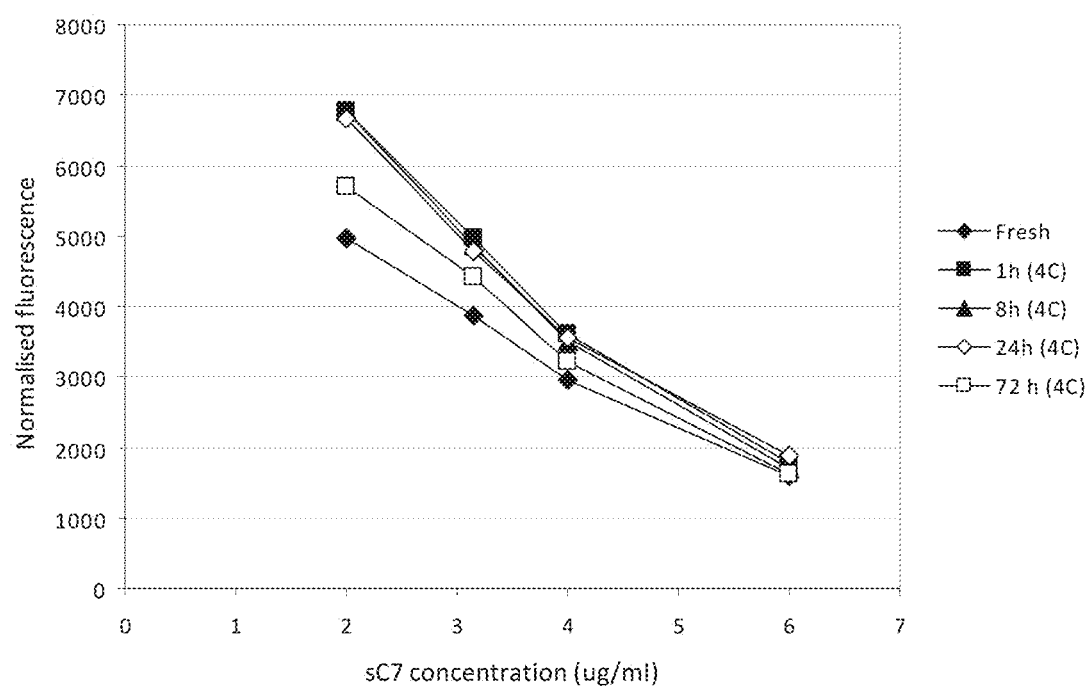

FIG. 8. SYBR Green-DNA binding assay to quantify the stability of complexes formed with Compound 7 bolasomes and Sig TFD.

Figure 9A:
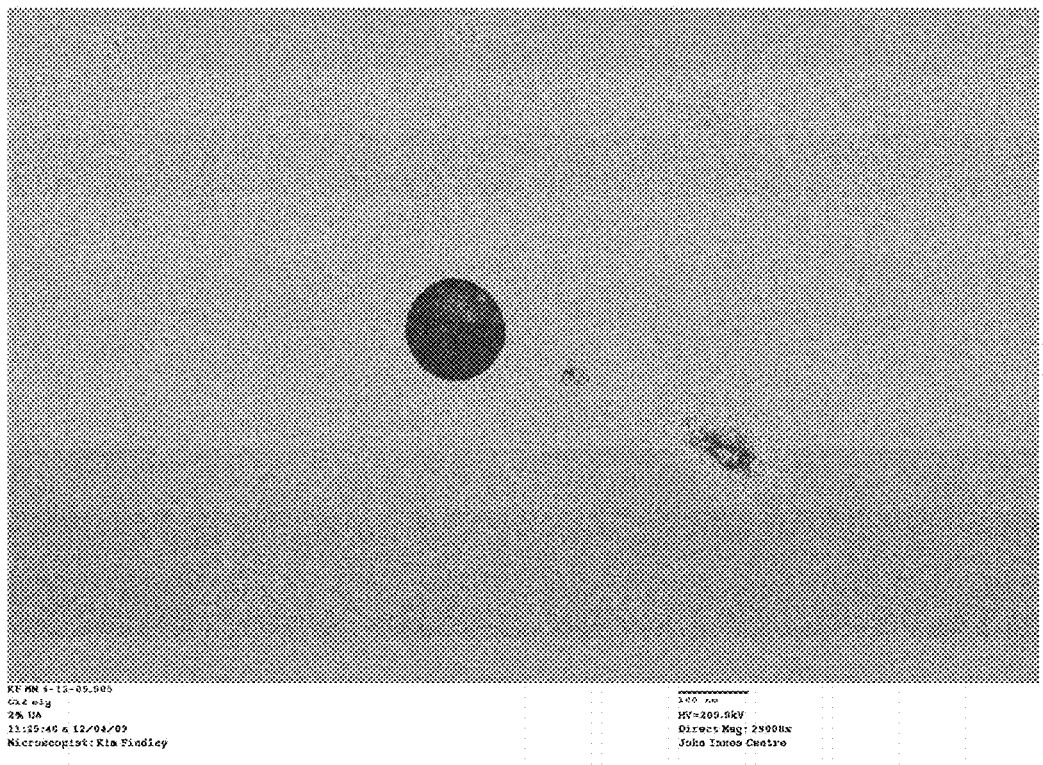
Figure 9B:
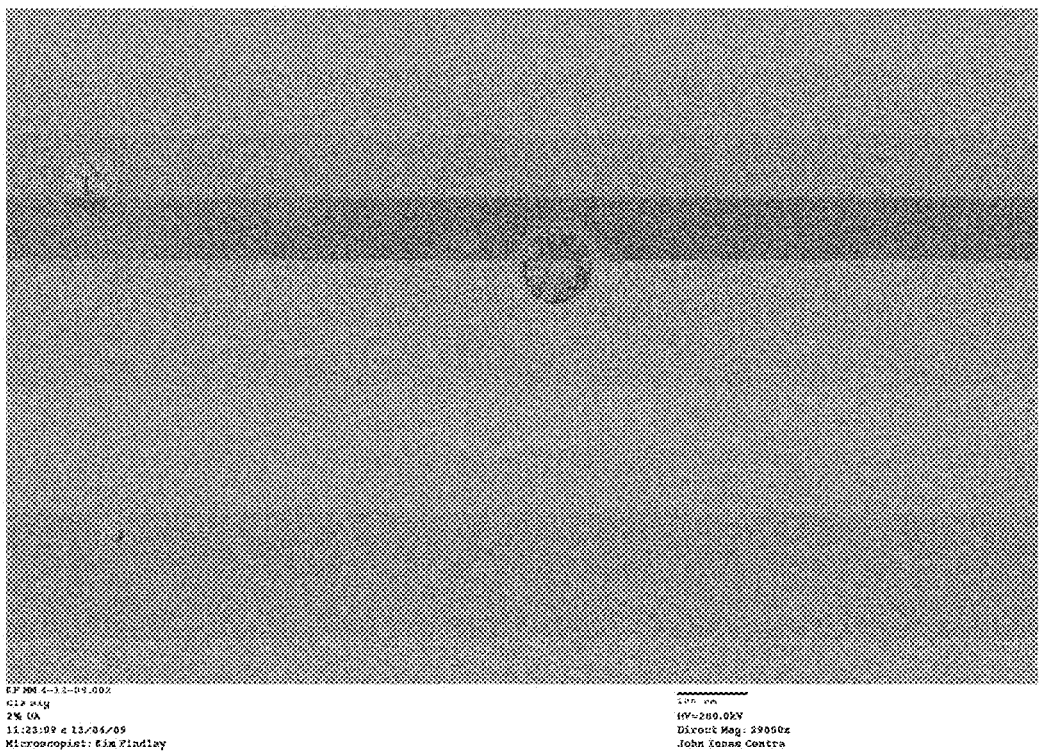

FIGS. 9A & 9B. Electron micrographs of TFD complexes formed with Compound 7 bolasomes and Sig TFD.

Figure 10:
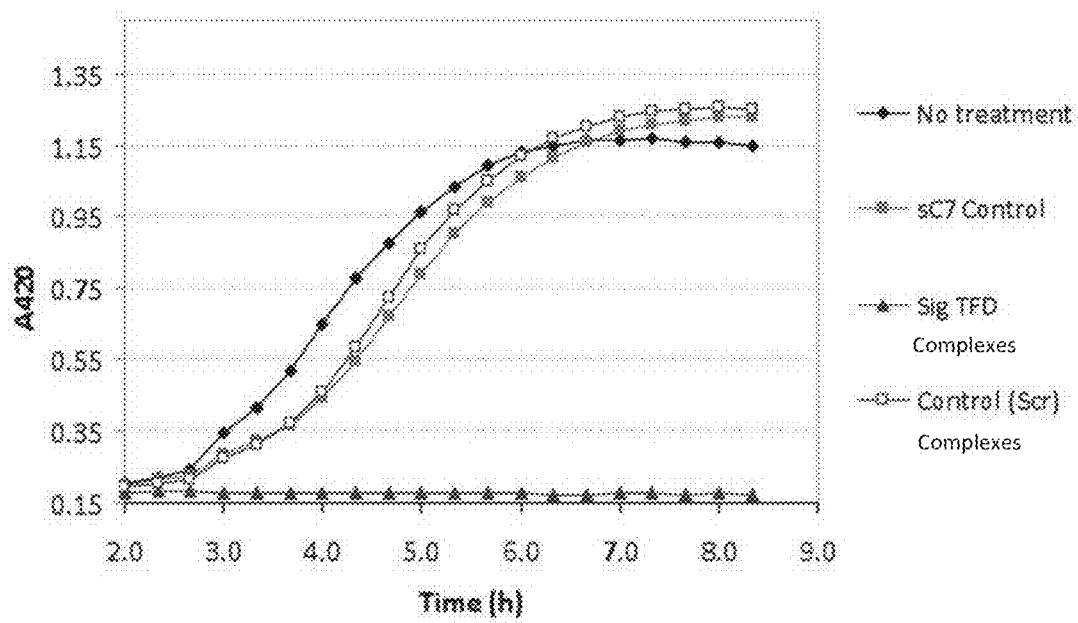

FIG. 10. In vitro bioassays demonstrating growth retardation of EMRSA-15 with Sig complexes formed with Compound 7.

Figure 11:
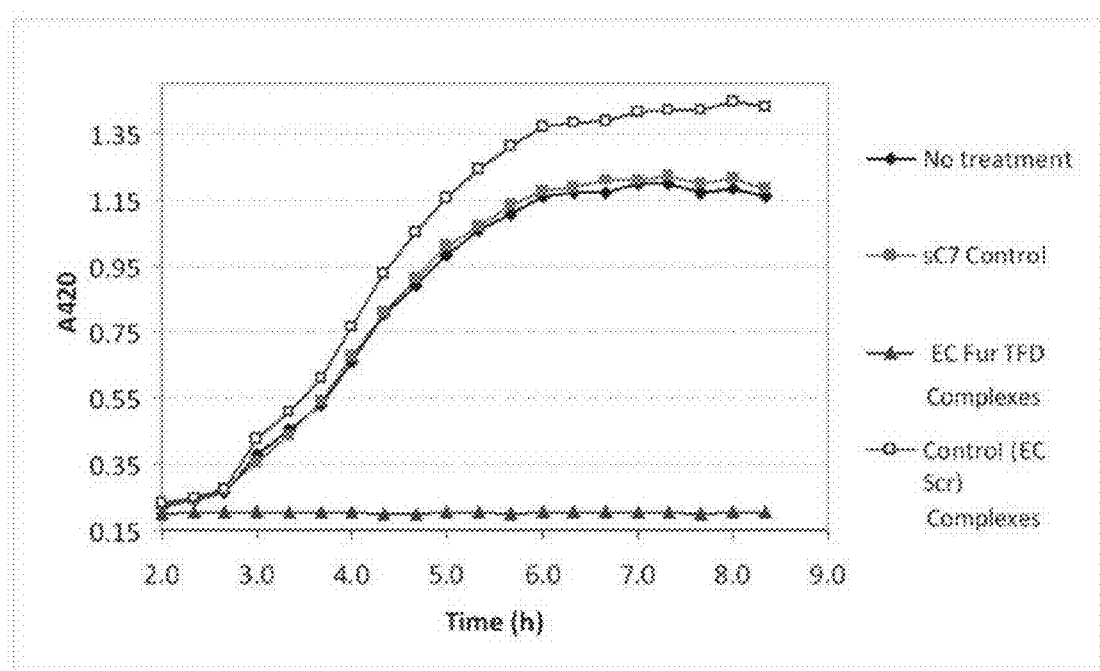

FIG. 11. In vitro bioassays demonstrating growth retardation of E. coli with EC_Fur complexes formed with Compound 7.

Figure 12:
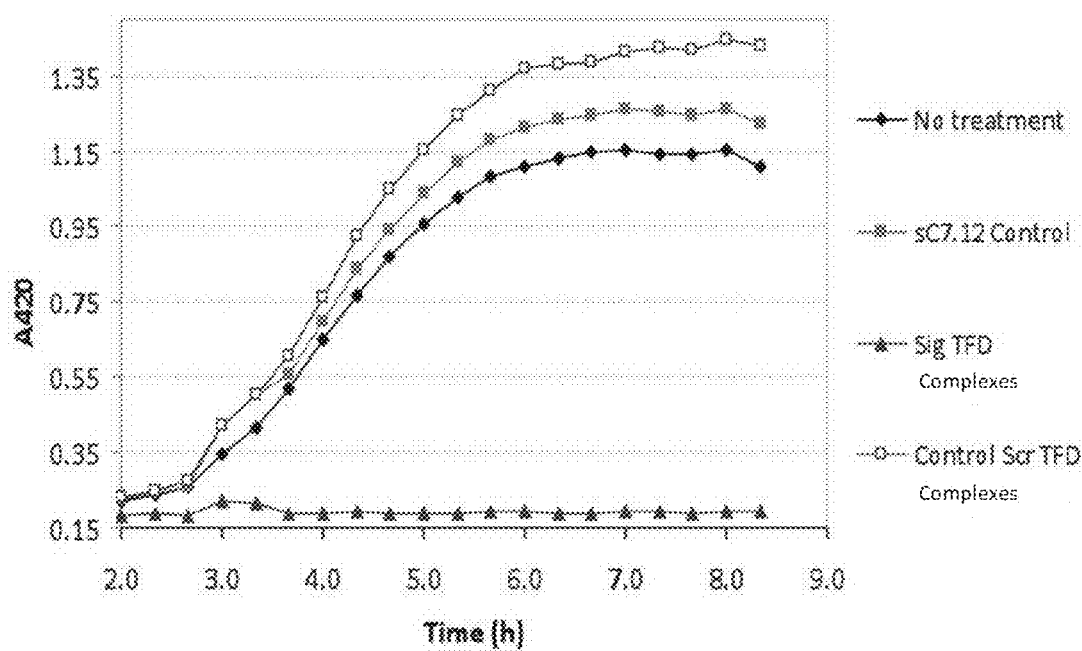

FIG. 12. In vitro bioassays demonstrating growth retardation of EMRSA-15 with Sig complexes formed with Compound 7_12.

Figure 13:
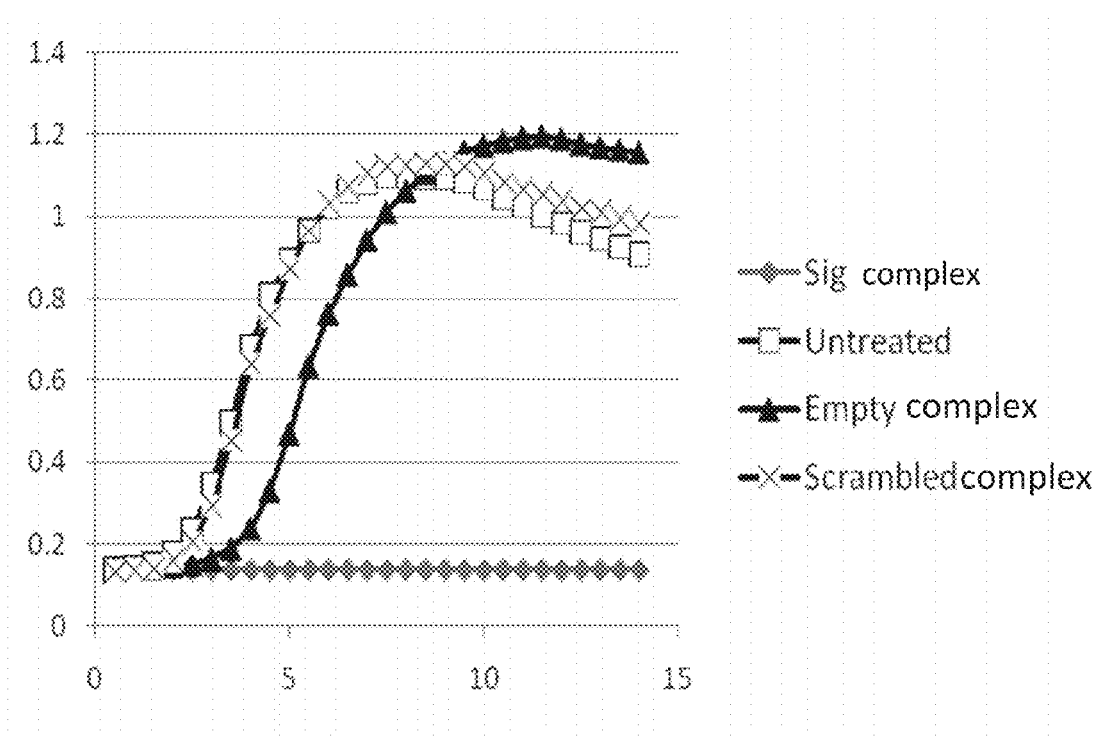

FIG. 13. Graphs of time elapsed against optical density showing the effect of a hairpin Sig TFD/Compound 7_12 complex vs a Scrambled complex and an Empty control on the growth of the MRSA strain.

Figure 14:
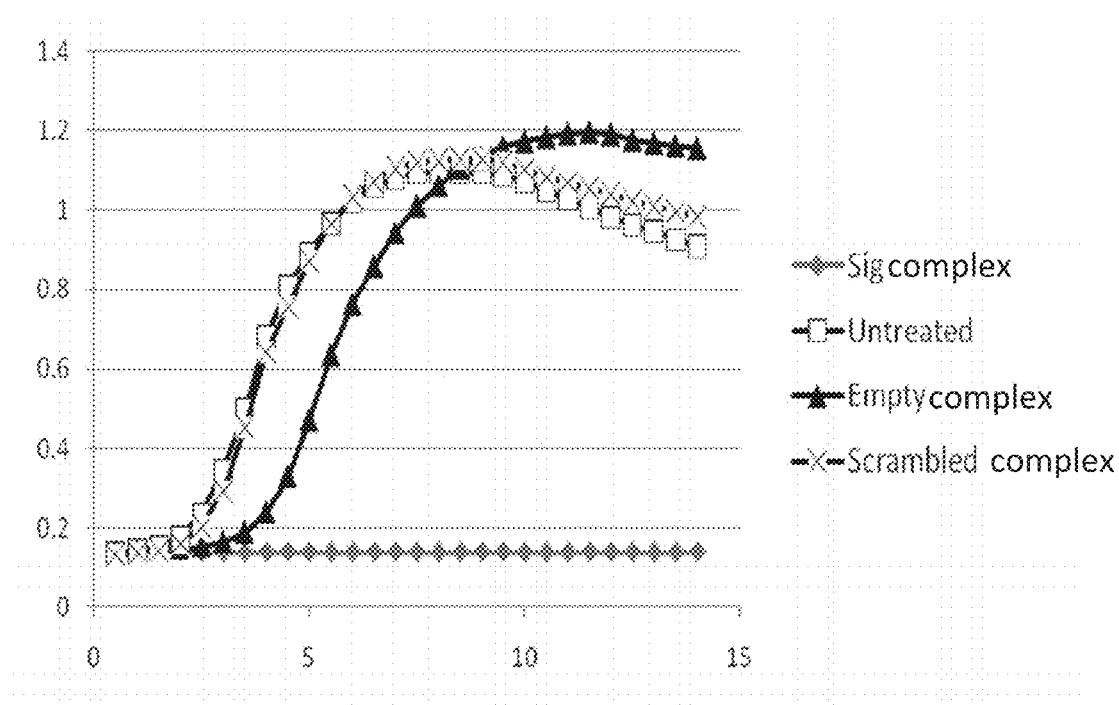

FIG. 14. Graphs of time elapsed against optical density showing the effect of a hairpin Sig TFD/Dequalinium complex vs a Scrambled complex and an Empty control on the growth of the MRSA strain.

Figure 15:
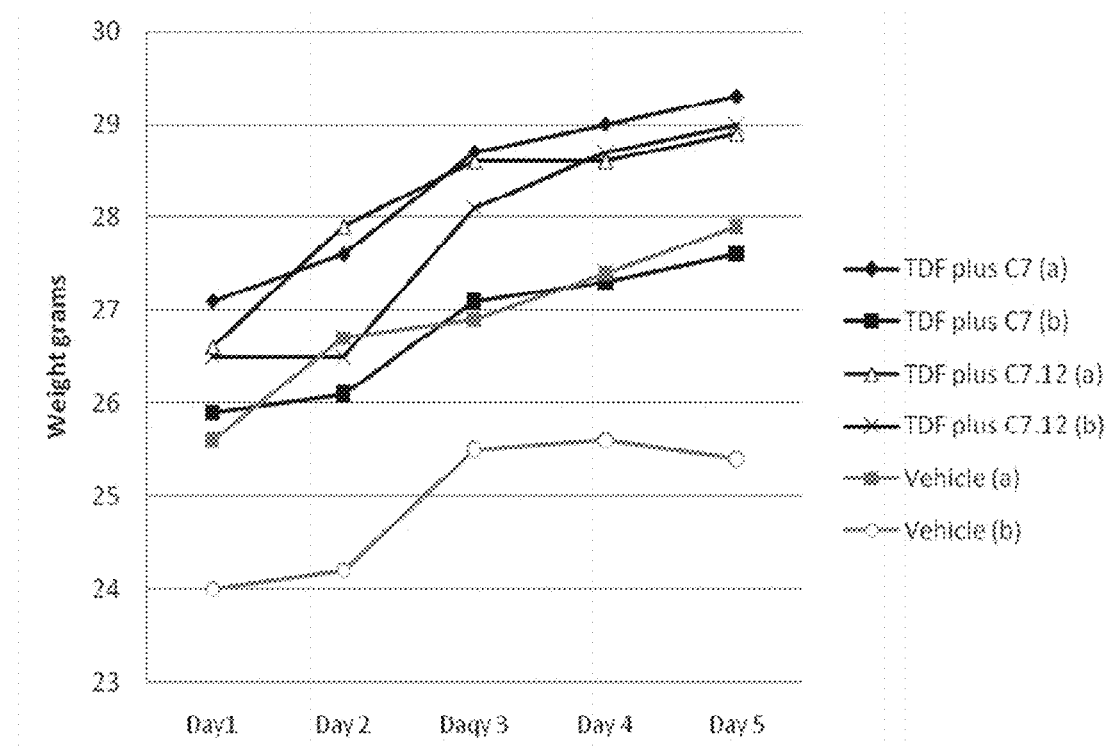

FIG. 15. Graph illustrating the weight gain of mice treated with SA_Sig TFD/Compound 7 complex, SA_Sig TFD/Compound 7_12 complex, or saline solution. a) and b) denote independent repeats of the experiment.

Figure 16:
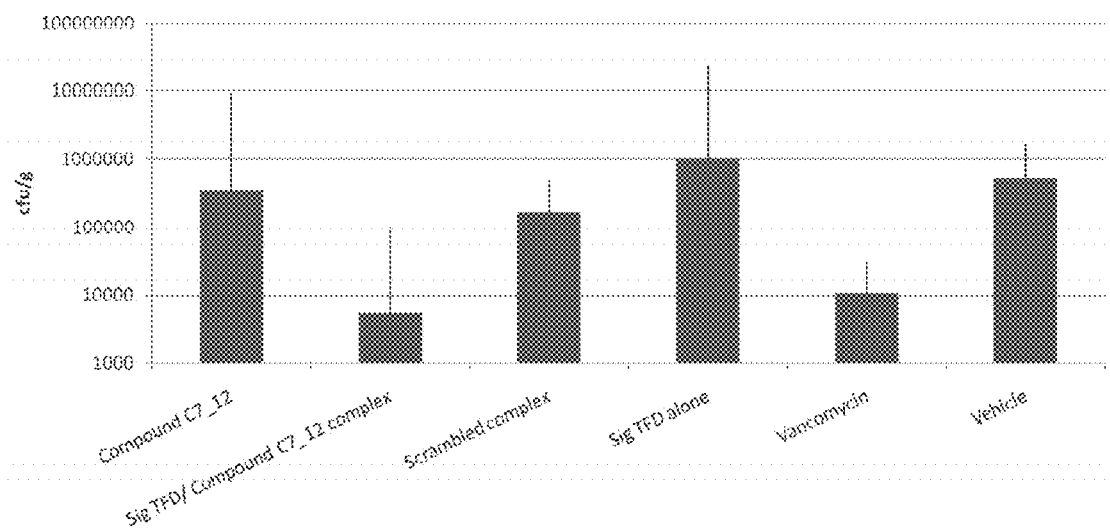

FIG. 16. Bar chart showing kidney tissue burden following treatment of mice with Compound 7_12, SA_Sig TFD/Compound 7_12 complex, SA_Sig_Scr TFD/Compound 7_12 complex, SA_Sig TFD, Vancomycin, or Vehicle.

Figure 17:
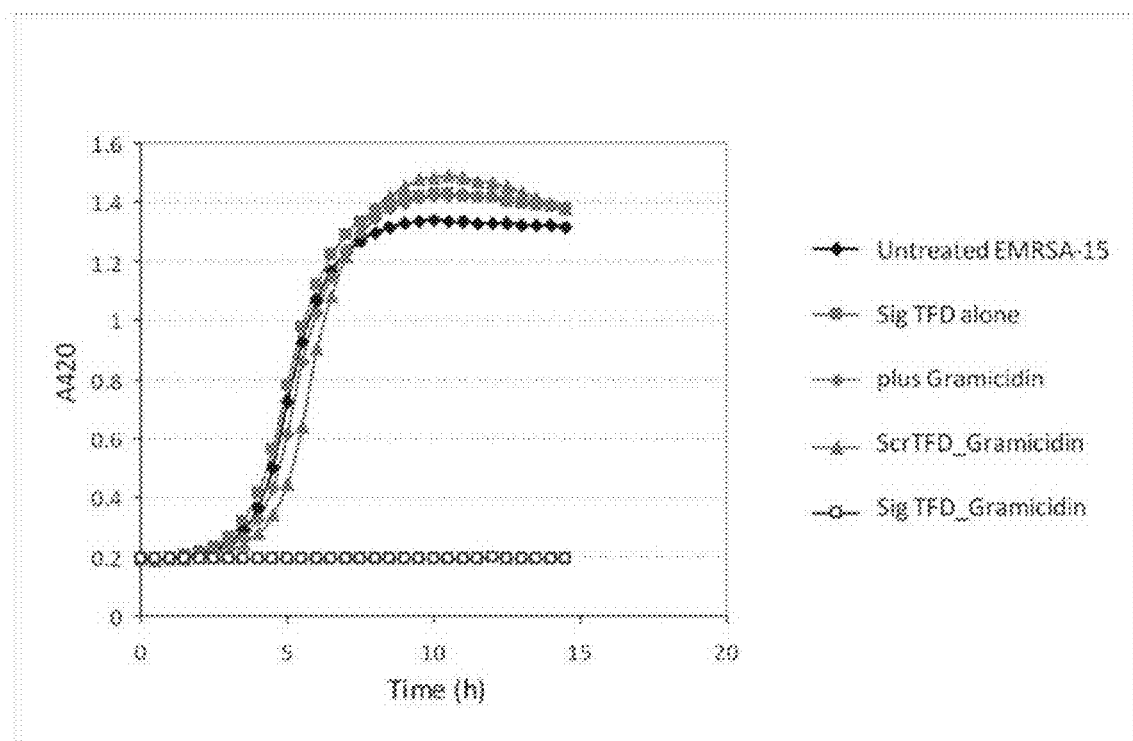

FIG. 17. In vitro bioassays demonstrating growth retardation of EMRSA-15 with Sig TFD mixed with Gramicidin.

Figure 18:
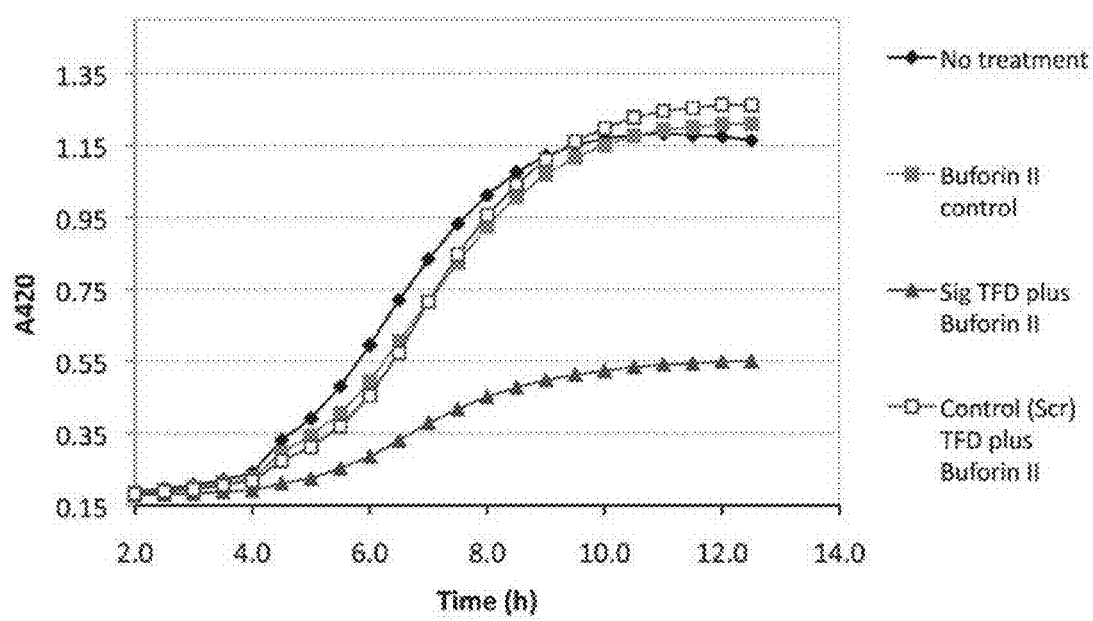

FIG. 18. In vitro bioassays demonstrating growth retardation of EMRSA-15 with Sig TFD mixed with Buforin II.

Figure 19:
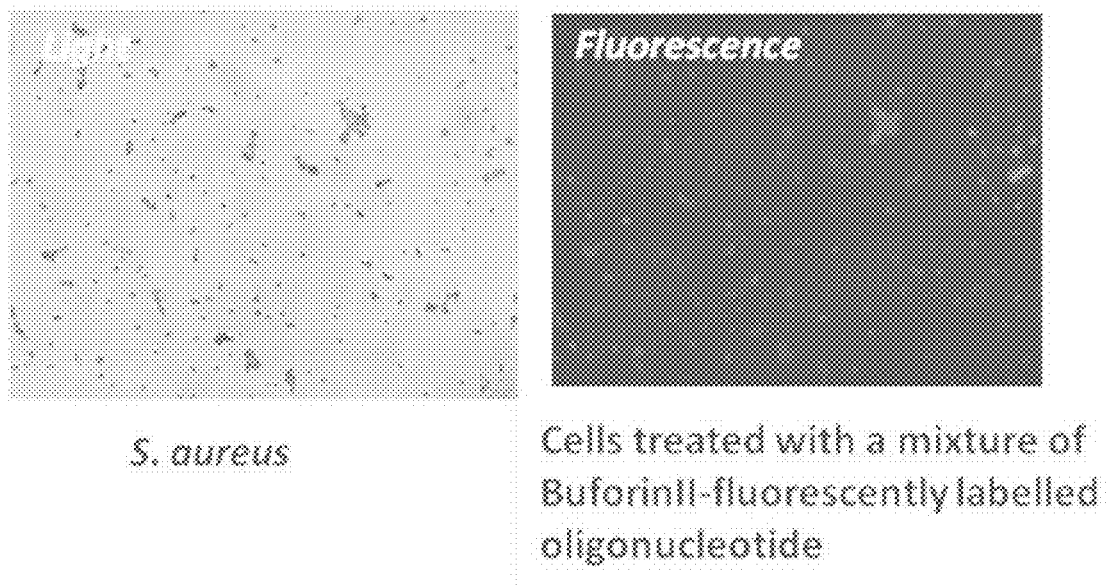

FIG. 19. Fluorescent microscopy confirms delivery of dye-labelled oligonucleotide to MRSA by Buforin II-derivatised complexes formed with Compound 7.

Figure 20:
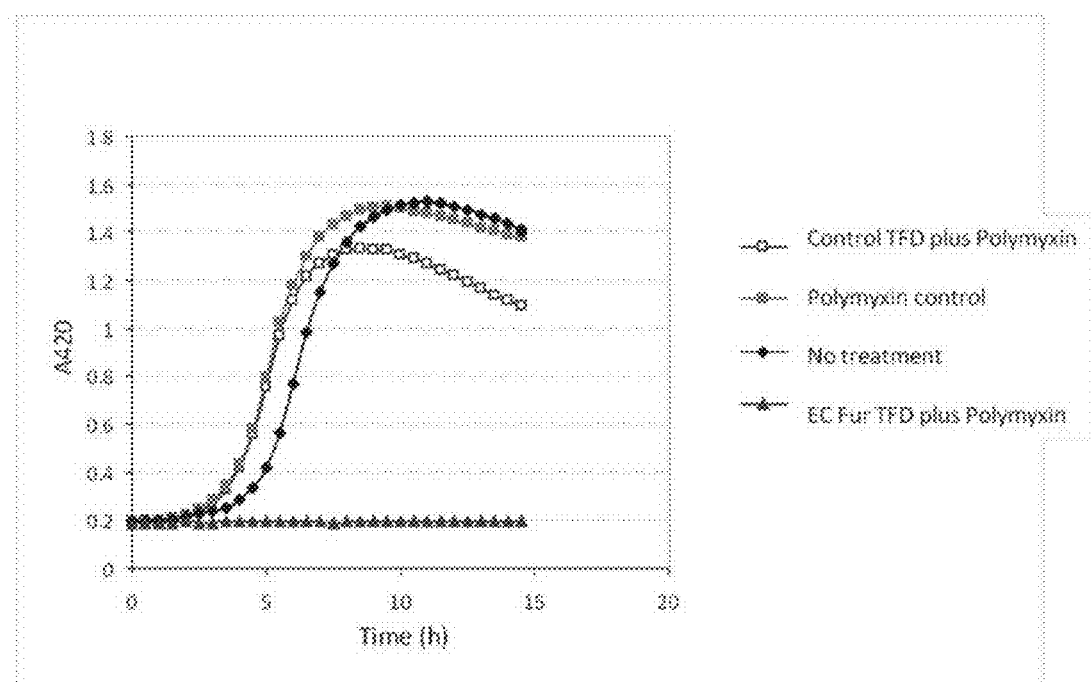

FIG. 20. In vitro bioassays demonstrating growth retardation of E. coli with EC_Fur TFD mixed with Polymyxin.

Figure 21:
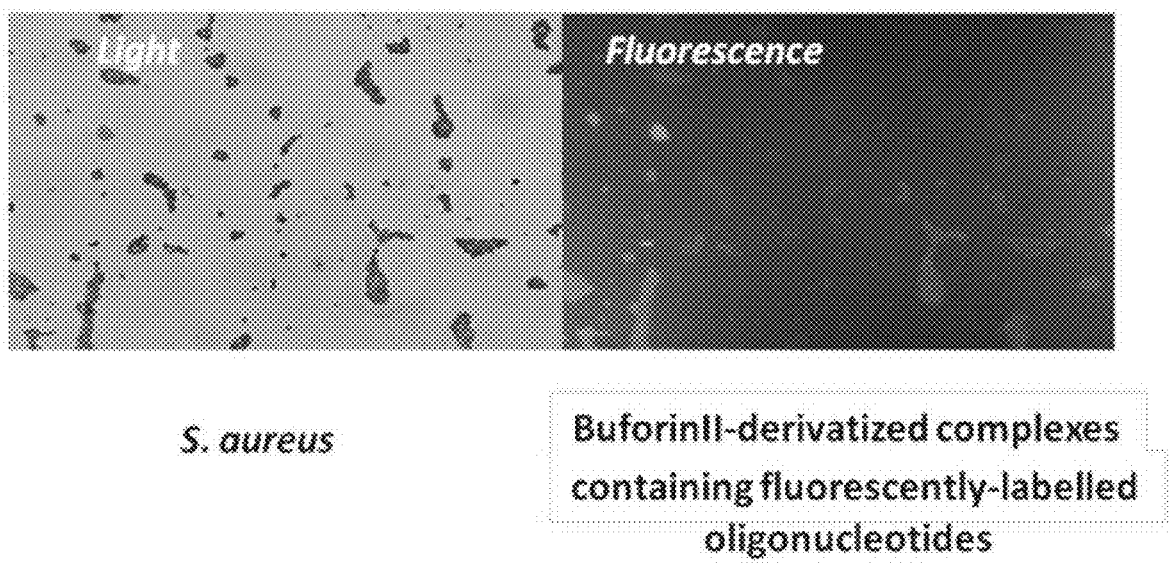

FIG. 21. Fluorescent microscopy confirms delivery of dye-labelled oligonucleotide to MRSA by Buforin II-derivatised complexes formed with Compound 7.

Figure 22:
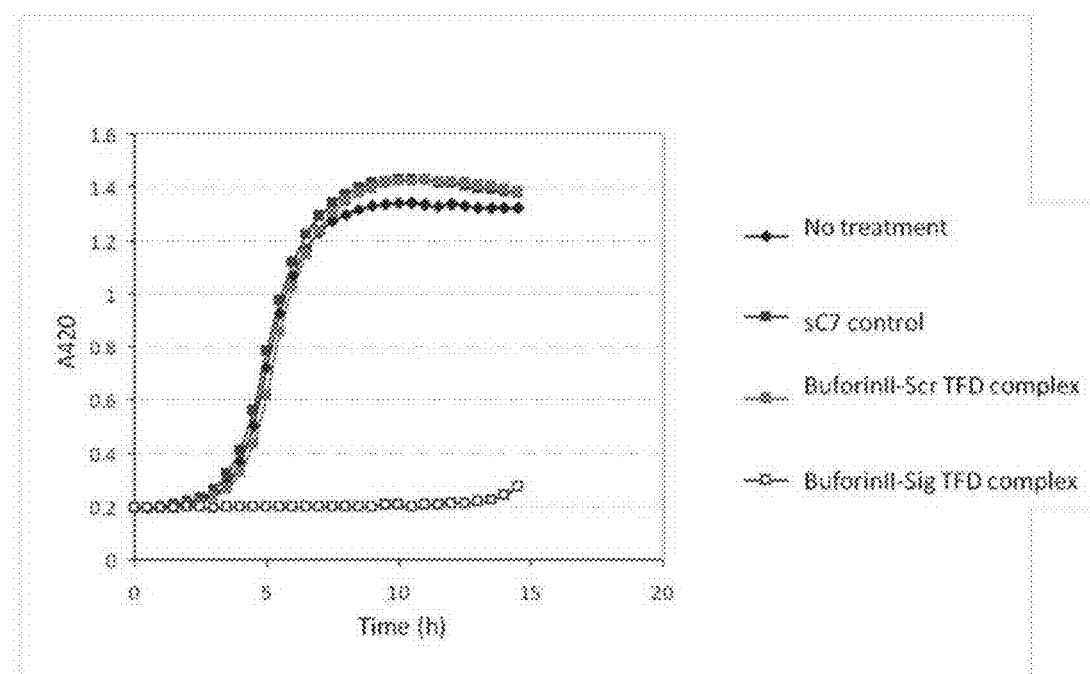

FIG. 22. In vitro bioassays demonstrating growth retardation of EMRSA-15 with Buforin II-derivatised Sig TFD complexes formed with compound 7.

BRIEF DESCRIPTION OF THE SEQUENCES

SEQ ID NO: 1—a native WhiB7 binding site in M. smegmatis str MC2 155
SEQ ID NO: 2—WhiB7 transcription factor decoy
SEQ ID NO: 3—a native FadR binding site in E. coli K12
SEQ ID NO: 4—FadR transcription factor decoy
SEQ ID NO: 5—a native binding site for YycF/YycG in S. aureus
SEQ ID NO: 6—a native binding site for YycF/YycG in S. aureus
SEQ ID NO: 7—LytM decoy
SEQ ID NO: 8—SsaA decoy
SEQ ID NO: 9—a native binding site for $Sig^B$ in S. aureus
SEQ ID NO: 10—a native binding site for $Sig^B$ in K. pneumoniae
SEQ ID NO: 11—a consensus sequence for Fur binding in S. aureus
SEQ ID NO: 12—a consensus sequence for Fur binding in E. coli
SEQ ID NO: 13—a native binding sequence for Fur in H. pylori
SEQ ID NO: 14—a consensus binding site for TcdR in C. difficile
SEQ ID NO: 15—a consensus binding site for Vfr in P. aeruginosa
SEQ ID NO: 16—a native binding site for Vfr in P. aeruginosa
SEQ ID NO: 17—a native binding site for Vfr in P. aeruginosa
SEQ ID NO: 18—a native binding site for NtrC in K. pneumoniae
SEQ ID NO: 19—a native binding sequence for ArsR in H. pylori
SEQ ID NO: 20—a native binding sequence for ArsR in H. pylori
SEQ ID NO: 21—a glycopeptide-resistant consensus sequence in S. aureus
SEQ ID NO: 22—an Agr binding motif in S. aureus
SEQ ID NO: 23—an Agr binding motif in S. aureus
SEQ ID NO: 24 & 25—forward and reverse primer sequences for PCR preparation of the SAsigB TFD
SEQ ID NO: 26 & 27—forward and reverse primer sequences for PCR preparation of the SAfhu TFD
SEQ ID NO: 28 & 29—forward and reverse primer sequences for PCR preparation of the SsaA TFD
SEQ ID NO: 30—phosphorylated Sig dumbbell TFD oligonucleotide sequence
SEQ ID NO: 31—phosphorylated Sig dumbbell TFD oligonucleotide sequence
SEQ ID NO: 32—phosphorylated oligonucleotide incorporating the binding site for WalR
SEQ ID NO: 33—phosphorylated oligonucleotide incorporating the binding site for WalR
SEQ ID NO: 34 & 35—forward and reverse primers for FabB promoter
SEQ ID NO: 36 & 37—forward and reverse primers for TFD containing the recognition sequence for the σ54 factor of K. pneumoniae
SEQ ID NO: 38—WalR TFD consensus sequence
SEQ ID NO: 39—SigB TFD consensus sequence
SEQ ID NO: 40—KP_Sig TFD sequence
SEQ ID NO: 41—KP_Sig TFD consensus sequence
SEQ ID NO: 42—Gram negative Sig TFD hairpin sequence
SEQ ID NO: 43 & 44—forward and reverse primers for scrambled S. aureus Sig binding site
SEQ ID NO: 45 & 46—forward and reverse primers used for amplification of a target sequence from the pGEMT-Easy vector
SEQ ID NO: 47 & 48—forward and reverse primers for WhiB7 TFD
SEQ ID NO: 49—SA SIG hairpin TFD sequence
SEQ ID NO: 50—SA_SIG scrambled hairpin TFD sequence
SEQ ID NO: 51—Buforin II peptide sequence
SEQ ID NO: 52—Tef-derivatised SASig TFD

EXAMPLE 1

Formation of Complexes with Dequalinium Analogues and TFDS

Weissig et al have shown (WO99/013096) that dequalinium (DQA) can be used to deliver DNA to mitochondria. With sonication, DQA forms spheric-appearing aggregates with a diameter of between about 70 and 700 mm, which is similar to phospholipids vesicles. These aggregates were termed DQAsomes' in WO99/013096 and 'bolasomes' in Weissig and Torchilin ((2001) Adv. Drug Delivery Rev. 49: 127-149). The term 'bolasome' is used in this specification to describe vesicles of DQA and its analogues after the compounds have been subjected to sonication.

Complexes consist of a Transcription Factor Decoy (TFD) oligonucleotide self-assembled with a suitable delivery compound. A TFD oligonucleotide is 40 to 100 nucleotides in length and has a natural phosphate backbone. It self anneals to form a binding site for the targeted transcription factor and has a naturally-forming hairpin to protect the 5' and 3' ends, an example of which is shown below (GN_SIG_HP):

```
                                        SEQ ID NO: 42
      -agc-gtg-ata-atc-att-atc-g- agcg5'                           g

3'-cac-tat-tag-taa-tag-a-
```

In an alternative configuration, small hairpin loops at either end of the TFD act to protect the molecule from degradation and give the TFD a dumbbell (DB) shape.

Materials and Methods.

Preparation of Delivery Compounds.

15 mg of each compound (Sygnature Ltd.) was dissolved in 10 ml methanol and dried to completion using a rotary evaporator and re-suspended in 5 mM Hepes pH7.4 to a final concentration of 10 mM. Compound 7 dissolved readily to give a clear, light yellow solution. Compound 7_12 dissolved after being place in a sonicator bath for 1 h, forming an opaque, light yellow solution. Both solutions were subjected to probe sonication on ice using an MSE Soniprep 150. The conditions used were: 60 cycles of 30 s on (amplitude 10 microns) and 60 s off. Following this treatment, the Compound 7_12 sample was entirely clear. Both samples were centrifuged to remove debris and are referred to as sC7 (sonicated Compound 7) or sC7_12 (sonicated Compound 7_12). This step formed vesicles or bolasomes'.

Preparation of Dumbbell TFD Complexes.

2 µg of TFD (a 32 by oligonucleotide which has been ligated to form a monomeric circle) was mixed with 1 ml of either 5 mM Hepes pH7.4 buffer or LB broth (Luria Bertani broth: 1% (w/v) Bacto-tryptone, 5% (w/v) Bacto-Yeast Extract, 5% (w/v) NaCl) which was then mixed with between 1 and 10 µl of either sC7 or sC7_12 at room temperature.

Preparation of Hairpin TFD Complexes.

Oligonucleotides were suspended in water at a concentration of 1 mM (i.e. 180 nmoles in 180 µl. The suspension was diluted to 10 µM in water and heated to 95° C. for 2 mins in dry heating block, after which the suspension was removed from the heat and allowed to cool to room temperature. To confirm that the TFD had annealed properly, 1 µl TFD was mixed with 1 µl 10×NEB Buffer 1, 6 µl water and 1 µl Exonuclease I (NEB). A control mixture excludes the 1 µl TFD. The mixture was incubated at 37° C. for 30 min before being separated on a 3% Low Melting Point agarose gel/TAE stained with 0.5×SYBR Green. Correct TFD conformation was confirmed by resistance to exonuclease digestion.

To prepare delivery complexes, 10 mg of compound was suspend in 12.5 ml of 5 mM Hepes pH7.5 (final concentration 0.8 mg/ml) and dissolved by sonication (30×30 s on, 30 s off, on ice at 10µ). Absorbance of the resulting solution was measured at 327 nm to establish an accurate concentration. 12.5 µl delivery compound was mixed with 40 µl 10 µM TFD and 447.5 µl 5 mM Hepes (pH7.5) and sonicated in an ice bath using an MSE 150 Soniprep attached with a microprobe. Thirty cycles of sonication were performed with 30 s on (with 50% power, approximately 10µ) and 30 s off.

DNA Binding Assays.

To determine the proportion of TFDs being bound by the vesicles, a SYBR-green binding assay was used. TFD complexes were formed as described above in Hepes buffer with the adaptation that the buffer contained 5 µl of a 1 in 10 dilution of SYBR Green I dye (Invitrogen, 10,000× stock prepared in DMSO). Fluorescence was measured ($\lambda_{EX}$ 497 nm, $\lambda_{EM}$ 520 nm) to determine how much bolasome needed to be added to quench the binding of SYBR Green to the TFDs.

Size Determination.

The size of the bolasomes was determined by Dynamic Light Scattering using a Dynapro Titan DLS Instrument.

Visualisation of Particles.

The size of the particles was measured using electron microscopy. Samples were directly stained with uranyl acetate before imaging.

Results.

1.1 Size Distribution of sC7 Bolasomes sC7 bolasomes were prepared in 5 mM Hepes buffer at a concentration of 10 mM. Prior to measurement of their size distribution by dynamic light scattering the bolasomes were diluted in the same buffer 1000-fold. The majority of the material by mass had a diameter in excess of 3 µm and was caused by non-specific aggregates or dust. The remaining particles had an average diameter of 68 nm (FIG. 4). This is somewhat different to the published size distribution of the vesicles (Weissig et al. 2001 S. T. P. Pharma Sci. 11: 91-96: Table I, see Compound 7) which estimated the size distribution to be 169 nm+/−50 nm and commented that the distribution was tight. The values for sC7 bolasomes are closer to the published values, although the difference may reflect different experimental parameters and measurement instruments. Indeed, the fact that the sC7 bolasomes were stable despite dilution indicates that they have increased stability over bolasomes formed by sonication of dequalinium solutions, as these revert to the monomer on dilution (which has a diameter of less than 10 nm).

The diameters of sC7 and sC7_12 bolasomes (see 1.2) are tabulated in Table 2:

TABLE 2

Calculated values of minimum concentrations of sC7 and sC7_12 bolasomes needed to quench SYBR Green-binding to a fixed concentration of TFD.

| Item | Diameter (nm) | % Mass |
|---|---|---|
| sC7 bolasomes | 68.0 | 100 |
| Peak 1 | | |
| sC7_12 bolasomes | 48.4 | 27.2 |
| Peak 1 | 197.7 | 72.8 |
| Peak 2 | | |

1.2 Size Distribution of sC7_12 Bolasomes sC7_12 bolasomes were prepared in 5 mM Hepes buffer at a concentration of 10 mM. Prior to measurement of their size distribution by dynamic light scattering the bolasomes were diluted in the same buffer 1000-fold. As described in 1.1, the signal from the large material was discounted. The remaining particles had average diameters of either 48.4 nm or 197.7 nm and were present in a ratio of 1:2.5 (FIG. 5). This was markedly different from the diameters of the sC7 bolasomes. However, the particles had a better size distribution than reported by others for those formed with similar concentrations of dequalinium and were comparable to those obtained by Weissig for bolasmomes formed from Compound 7 (Weissig et al. (2001) S. T. P. Pharma Sci. 11:91-96).

1.3 Establishing Optimum Binding Conditions of sC7 and sC7_12 to TFD with DNA-Binding Assay SYBR-Green I dye binds specifically to double-stranded DNA and, as it does, gives a strong fluorescent signal. By measuring the change in signal in the presence of different concentrations and types of bolasome, it was possible to calculate the minimum amount of bolasome needed to quench the SYBR-Green binding, due to the dye being excluded by the bolasomes. This was achieved by extrapolation from the linear portion of a titration curve that plotted amount of bolasome added to fluorescent signal. Using a fixed concentration of 2 μg TFD/ml, the minimum concentration of sC7 bolasome was found to be 6.13 μg/ml (FIG. 6). At these concentrations no quenching was seen by the monomeric C7.

The minimum concentration for the sC7_12 bolasomes was found to be 9.26 μg/ml (FIG. 7).

The minimum amount of bolasome required was used in the preparation of TFD complexes. Such concentration was also used to ensure that there was as little sample to sample variation as possible between the preparations of bolasomes. In general, variation of approximately 20% was seen and had no observable affect on biological function.

The stability of the complexes was measured by monitoring the normalised fluorescence due to SYBR Green dye binding. The titration curves for TFD complexes formed with sC7 bolasomes remained constant for excess of 72 h when stored at 4° C. (FIG. 8), showing that the conditions illustrated here provide a substantial improvement in the stability of the complexes formed.

1.4 Electron Micrograph Imaging of sC7 Bolasomes and TFD Complexes

The TFD complexes formed between the sC7 bolasome and a TFD were visualised by electron microscopy by negative staining with uranyl acetate. Two examples are shown in FIGS. 9A and 9B. Round particles of between 50 and 100 nm were clearly seen with densely staining interiors with granules evident in the interior that may be condensed bodies of DNA.

EXAMPLE 2

Delivery of TFD in Compound 7 Bolasome Kills MRSA

Materials and Methods

Preparation of TFD Dumbbells by Ligation (DB-TFD)

Two oligonucleotides were synthesised, each containing one strand of the recognition site for the *S. aureus* alternative sigma protein. At either end of the molecule a small hairpin loop acted to protect the molecule from degradation. Each oligonucleotide was re-suspended in $dH_2O$ at a concentration of 250 pmol/μl. To form the Sig dumbbell TFD (referred to as Sig TFD) the following phosphorylated oligonucleotides were synthesised:

```
                                      SEQ ID NO: 30
SigDB1: P-CTT GGT TTT TCC AAG GAA GAT TAG AAA TTA

TTT CGA TGG GTA TAT AAT A

SEQ ID NO: 31
SigDB2: P-CCG TCT TTT TGA CGG TAT TAT ATA CCC ATC

GAA ATA ATT TCT AAT CTT C
```

When annealed, these formed the following molecule:

```
   T CCAAG gaa gat tag aaa tta ttt cgat ggg tat ata ata PCCGTC T

TTT                                                         TTT

T GGTTCPCTT CTA ATC TTT AAT AAA GCTA CCC ATA TAT TAT GGCAG T
```

30 μl of each oligonucleotide was mixed with 27 μl of $dH_2O$ and annealed using the following PCR programme: ANNEAL: 95° C. 3 min, cool at −0.1° C./s to 8° C., end. Following which, 10 μl of 10×NEB Ligase buffer and 3 μl HC T4 DNA ligase (NEB) were added. The mixture was incubated overnight at 16° C. The material was then extensively digested with T7 exonuclease (NEB) to remove any unligated oligonucleotides and then recovered by two rounds of ethanol precipitation. A DB_TFD was also prepared containing a scrambled version of the Sig binding site, referred to as Scr TFD. In this instance the phosphorylated primers used were:

```
                                          SEQ ID NO: 43
SigScr_SA1: CTT GGT TTT TCC AAG TAG AAA GAA GAT

TTA GGG CGA T TTT ATA ATA TAT

SEQ ID NO: 44
SigScr_SA2: CCG TCT TTT TGA CGG ATA TAT TAT AAA

ATC GCC CTA AAT CTT CTT TCT A
```

Formation of Complexes

The minimum amount of sC7 bolasome needed to bind 2 μg of either TFD was established empirically and the appropriate amount of bolasome was mixed with the TFDs in 5 mM Hepes, pH7.4, to form complexes. Dilutions of the TFD nanoparticle were used in subsequent bioassays.

Performing Growth Studies in 96-Well Plates

A growth assay was performed using complexes consisting of either the Sig TFD or Scr TFD mixed with sC7 bolasomes, to determine the effect on growth of a clinically-isolated MRSA strain. The assays to determine the effect on growth of bacterial cells were performed using 96 well plates, each well containing 200 μl of broth consisting of LB media. 1 μl of various concentrations of TFD complexes was added to each well and the effect on bacterial growth of *S. aureus* was monitored by measuring absorbance of the broth at intervals during incubation. The plates were incubated at 37° C. with shaking and absorbance readings (at 450 nM) were taken using a plate reader.

Results 2.1 Tfd Complexes can Efficiently Kill MRSA In Vitro

TFD complexes were prepared with sC7 bolasomes using a TFD known to kill MRSA cells called 'Sig TFD' or a scrambled version as a control, 'Scr TFD'. The MRSA strain, EMRSA15, was used to inoculate LB broth to provide a final concentration of cells of $5\times10^5$/ml. 200 μl aliquots were dispensed into wells in a 96 well plate. Wells were supplemented with varying concentrations of Sig TFD complex, Scr TFD complex, equivalent concentrations of the sC7 bolasomes as a control for any antibacterial effect of the dequalinium analogue (sC7 control) or the wells were untreated (FIG. 10). Both TFD complexes contained sC7 at a concentration of 500 ng/ml and TFDs at 5 μg/ml. The sC7 control consisted of bolasomes at a concentration of 500 ng/ml.

Cell growth was essentially similar for the untreated sample, the sC7 control and the Control Complex (consisting of the Scr TFD). However, the Sig TFD complex prevented bacterial growth. Hence, the combination of the sC7 bolasome with the Sig TFD killed the MRSA strain, whereas the control TFD complex did not. This was due to the complexes effectively delivering the TFD therapeutic to the MRSA. The action of delivery alone, with concomitant membrane damage, did not kill the bacteria as neither the Control Complex nor an equivalent amount of sC7 bolasomes affected cell growth.

EXAMPLE 3

Delivery of TFD by Compound 7 Bolasome Kills *E. coli*

Materials and Methods

Preparation of Fur TFDs by PCR

Fur TFDs were designed to incorporate the binding site for the transcriptional regulator of fatty acid synthesis enzymes, FadR, which occurs upstream of the FabB gene in *Escherichia coli*. The FabB gene encodes an enzyme involved in fatty acid synthesis (*J. Bacteriology* (2005) 183:5292). The oligonucleotides used to amplify the promoter sequence were:

```
                                        SEQ ID NO: 34
fabBf 5'-tct tta aat ggc tga tcg gac ttg-3'

SEQ ID NO: 35
fabBr 5'-agt aag ttt cga atg cac aat agc gta-3'
```

The resulting fragment was ligated into pGEMTEasy vector (Promega) and PCR TFDs were synthesized by PCR amplification using oligonucleotide primers designed to anneal to the backbone of the vector immediately flanking the insert, for example:

```
                                        SEQ ID NO: 45
    TEf: 5'-ggc cgc cat ggc ggc cgc ggg aat tc-3'

SEQ ID NO: 46
    TEr: 5'-agg cgg ccg cga att cac tag tg-3'.
```

The PCR product is ethanol precipitated and re-suspended in TE buffer (10 mM Tris.HCl, 1 mM EDTA pH8.0) at a concentration of 500-1000 ng/µl.

A control TFD having a the sequence that gave rise to a similar sized PCR fragment when used in an amplification reaction with genomic DNA isolated from *Mycobacterium smegmatis* was also generated. The sequences of these oligonucleotides were:

```
                                        SEQ ID NO: 47
    WhiB7.f CAC CAG CCG AAA AGG CCA CGG

SEQ ID NO: 48
    WhiB7.r CAA AAA TGG CCA CGG ATC CGG GTG
```

Results 3.1 TFD Complexes can Efficiently Kill *E. coli* In Vitro

TFD complexes were formed with a TFD known to be active against *E. coli*, EC Fur, and a control TFD, EC FurScr TFD. The experiment was performed as described in Example 2.1 and similar results were obtained (FIG. 11). Again, the results show that complexes formed with sC7 bolasomes and EC Fur TFD prevented growth of *E. coli* (strain DH10B) in an iron-limited media.

EXAMPLE 4

Delivery of TFD by Compound 7_12 Bolasome Kills MRSA

Materials and Methods

TFD complexes were formed as described in Example 2 with Sig TFD or Scr TFD, with the exception that sC7_12 bolasomes were used. The resultant TFD complexes were tested for their activity in preventing growth of MRSA strain EMRSA15.

Results 4.1 Tfd Complexes can Efficiently Kill MRSA In Vitro

TFD complexes were prepared using a TFD known to kill MRSA cells called 'Sig TFD' and a scrambled version, 'Scr TFD', as a control with sC7_12 bolasomes. The MRSA strain, EMRSA15, was used to inoculate LB broth to give a final concentration of cells of $5 \times 10^5$/ml. 200 µl aliquots were dispensed into wells in a 96 well plate. Wells were supplemented with varying concentrations of Sig TFD complexes, Scr TFD complexes, equivalent concentrations of the sC7_12 bolasomes as a control for any antibacterial effect of the dequalinium analogue (sC7_12 control) or the wells were untreated (FIG. 12). Both TFD complexes contained sC7_12 at a concentration of 800 ng/ml (1.3 µM) and TFDs at 5 µg/ml (153 nM). The sC7_12 control consisted of bolasomes at a concentration of 800 ng/ml.

Cell growth was essentially similar for the untreated sample, the sC7_12 control and the control complex (including the Scr TFD). However, the Sig TFD complex prevented bacterial growth. Hence, the combination of the sC7_12 bolasome with the Sig TFD killed the MRSA strain, whereas the control TFD complex did not. This was due to the complexes effectively delivering the TFD therapeutic to the MRSA. The action of delivery alone, with concomitant membrane damage, did not kill the cells as neither the control complex nor an equivalent amount of sC7_12 bolasomes affected cell growth.

EXAMPLE 5

Delivery of Hairpin TFD by Various Delivery Compounds Kills MRSA

TFD complexes containing the hairpin TFD SA SIG and either dequalinium, Compound 7 or Compound 7_12 were prepared using the method set out in Example 1. The size distributions of the formed vesicles were measured using a Malvern Nanosizer using standard methodology and are set out in Table 3 below:

TABLE 3

| Delivery Compound | Vesicle size distribution (nm) | Concentration (µM) |
|---|---|---|
| Dequalinium | 75-820 | 745 |
| Compound 7 | 139 +/− 35 | 75 |
| Compound 7_12 | 117 +/− 32 | 75 |

The size distribution of the vesicles was found not to alter when TFDs of different sequences were used. The sequence of the SA SIG HP (targeted to bind to the alternative sigma factor in *Staphylococcus aureus*) is:

```
                                               SEQ ID NO: 49
5'-gcg aag cga aga tta gaa att att tcc atg ggt ata taa tac ttg gtt ttt cca agt att ata tac cca tgg aaa taa ttt cta atc ttc-3'
```

5.1. Efficacy of SA_SIG_HP TFD Complexed with Compound 7_12

The TFD complex was prepared as described in Example 1 (referred to as Sig) as were two control snares, one containing no TFD (Empty) and the other a scrambled version of SA SIG HP (Scrambled) that contained the TFD SA_SIG_Scr_HP, which has the following sequence:

```
                                               SEQ ID NO: 50
5'-gcg aag cat ctt gta tgc aaa tag aat gaa taa tag ttt gac ttg gtt ttt cca agt caa act att att cat tct att tgc ata caa gat-3'
```

1 µl of each delivery complex was added to 200 µl of LB broth inoculated with 1 µl of a glycerol stock of an MRSA strain, EMSRA15, at a concentration of 3×10⁶ colony forming units per µl. The cultures were grown at 37° C. with mild shaking and the optical density of the cultures measured in a plate reader at half hour intervals.

The plots of time elapsed against optical density shown in FIG. 13 demonstrate that the Sig complex effectively prevented growth of the MRSA strain with concentrations of 500 ng/ml Compound 7_12 and 20 pmol TFD. Bacteria treated with the Scr complex (with similar concentrations of both Compound 7_12 and TFD) grew slower than both Empty control and the untreated sample. This has been observed in previous experiments and is interpreted as being due to growth being slowed by the action of delivering the scrambled TFD into the cell. When that TFD inhibits stress response, as does SA_SIG_HP, the cells fail to recover. Growth of the Empty control and the untreated sample were indistinguishable.

Hence, complexes containing the SIG_SA_HP TFD, designed to block essential pathways in *S. aureus*, are fatal to bacterial cells whereas delivery of a scrambled version of the TFD or the delivery vehicle alone is ineffective.

5.2. Efficacy of SA_SIG_HP Complexed with Dequalinium

The TFD complex was prepared as described in the section 5.1 above with the exception that the concentration of dequalinium used was 6-fold higher than the concentration of Compound 7_12. Similarly two control snares were prepared, one containing no TFD (Empty) and the other a scrambled version of SA SIG HP (Scrambled) that contained the TFD SA_SIG_Scr_HP.

1 µl of each delivery complex was added to 200 µl of LB broth inoculated with 1 µl of a glycerol stock of an MRSA strain, EMSRA15 at a concentration of 3×10⁶ colony forming units per µl. The cultures were grown at 37° C. with mild shaking and the optical density of the cultures measured in a plate reader at half hour intervals. The plots of time elapsed against optical density shown in FIG. 14 demonstrate that the Sig antibacterial effectively prevented growth of the MRSA strain with concentrations of 3 µg/ml Compound 7_12 and 10 pmol TFD. Bacteria treated with the Scr antibacterial (with similar concentrations of both Dequalinium and TFD) grew slower than both Empty control and the untreated sample. This has been observed in previous experiments and is interpreted as being due to growth being slowed by the action of delivering the scrambled TFD into the cell. When that TFD inhibits stress response, as does SA_SIG_HP, the cells fail to recover. Growth of the Empty control and the untreated sample were indistinguishable.

Hence, complexes containing the SIG_SA_HP TFD, designed to block essential pathways in *S. aureus*, is fatal to the cells whereas delivery of a scrambled version of the TFD or the delivery vehicle alone are ineffective.

EXAMPLE 6

Efficacy of SA Sig TFD by Compound C7_12 in Treatment of MRSA in a Mouse Sepsis Model Mice used in this study, male CD1 mice, were supplied by Charles River (Margate UK) and were specific pathogen free (16-18 g at delivery). All mice weighed 22-25 g at the beginning of the experiment.

6.1. Tolerability Study

Animals were treated in groups of two mice per treatment group, therefore six animals were used in total for the study. All the mice were weighed on day 1 of the study and placed randomly into boxes. The mice had the following treatments administered intravenously at 10 ml/kg:

100 µM SA Sig TFD (2 mg/ml; SEQ ID NO:9) and 525 µM (0.315 mg/ml) Compound 7 in saline solution;

100 µM SA Sig TFD (2 mg/ml; SEQ ID NO:9) and 525 µM Compound 7_12 (0.315 mg/ml) in saline solution; and saline solution alone.

The concentrations of TFD and delivery molecules were chosen to be approximately ten-fold greater than the predicted effective dose.

The mice were weighed daily post-treatment over a 100 h period before they were euthanised. The lungs, liver, spleen and kidneys were removed and visually examined and weighed. FIG. 15 shows the weight gain of all three groups with indices a) and b) referring to independent experimental repeats.

No significant difference was seen between the control treatments (saline) and those treated with combinations of TFD and delivery compounds. Thus, all treatments were well tolerated following intravenous administration. There were no acute events to report. Following treatment, mice fed and drank normally with no signs of distress. The weight increase of the treated mice was the same as the vehicle controls. Autopsy showed no gross abnormalities of kidneys, lungs, liver or GI tract. The weights of kidneys, lungs and liver were within the normal range. All test compounds are tolerated and suitable for further dosing up to the maximum dose used in this tolerability study.

6.2. Tissue Burden Study

Animals were treated in groups of since mice per treatment group, therefore forty eight animals were used in total for the study. Two 10 ml cultures of *Staphylococcus aureus* EMRSA 16 were prepared and placed on orbital shaker (220 rpm) overnight at 37° C. The following day, the *Staphylococcus aureus* EMRSA 16 cultures were removed from shaker, pelleted and washed twice before being resuspended in saline to an OD of 0.132 (1.5×10⁸ cfu/ml). This stock solution of *Staphylococcus aureus* EMRSA 16 was then further diluted 1:1.5 in saline (1×10⁸ cfu/ml) i.e. 2.0×10⁷ bacteria per mouse.

All forty eight mice were then infected with 0.2 ml of the 1.0×10⁸/ml suspension by intravenous injection into mouse tail vein. The number of *Staphylococcus aureus* EMRSA 16 bacteria per ml in the remainder of the suspensions after inoculation was also counted to confirm infection load.

Mice were treated 1, 9 and 17 hours post infection with either compound or vehicle, though vancomycin was only administered after 1 h. The treatments were a combination of antibiotic complexes, prepared with Compound 7_12 and various TFDs, as tabulated in Table 4 below.

TABLE 4

| Treatment | Compound C7_12 | SA Sig TFD | SA Scr Sig TFD | Vancomycin |
|---|---|---|---|---|
| C7_12 alone | 15 ng/kg | — | — | — |
| Sig complex | 15 ng/kg | 1 nM | — | — |
| Scr complex | 15 ng/kg | — | 1 nM | — |
| Sig TFD | — | 1 nM | — | — |
| Vancomycin | — | — | — | 25 mg/kg |
| Saline | — | — | — | — |

After 25 hours post infection, all animals were weighed and then euthanised. The kidneys were immediately removed and homogenised in ice-cold sterile phosphate buffered saline+0.05% Tween 80. Organ homogenates were quantitatively cultured onto CLED agar and incubated at 37° C. for up to 3 days and colonies counted. The data from the culture burdens was analysed by the Kruskal-Wallis test using Stats Direct.

6.3. Tissue Burden Study

The infectious dose administered was targeted at $3.7 \times 10^7$ bacteria per mouse to ensure that a relatively acute infection was established i.e. an infection that is sensitive to treatment. The mice were treated with systemic injection of either (A) the delivery compound alone (Compound C7_12), (B) 1 nM of SA Sig/Compound 7_12 complex, (C) 1 nM of Scrambled control complex, (D) 1 nM of SA Sig TFD alone, (E) vancomycin, used at a concentration sufficient to achieve a 2-fold reduction in colony forming units (cfu), or (F) vehicle. Following treatment, the mice were sacrificed and the burden found within the kidneys measured (see FIG. 16).

Statistical analysis of the results showed that the Sig snare antibacterial-treated mice achieved a similar reduction in burden to that achieved by vancomycin. All other controls show similar burdens to the vehicle treatment (Table 5).

TABLE 5

Statistical analysis of in vivo results. Kruskal-Wallis: all pairwise comparisons (Dwass-Steel-Chritchlow-Fligner) for Sig TFD complex

| Treatment | Sig complex | Scr complex | Sig TFD | Vancomycin | Vehicle |
|---|---|---|---|---|---|
| C7_12 | 0.0001 | 0.549 | 0.4695 | 0.0004 | 0.4109 |
| Sig snare | | 0.000 | <0.000 | 0.7263 | <0.0001 |
| Scr snare | | | 0.1894 | 0.0023 | 0.1588 |
| Sig TFD | | | | <0.0001 | 0.9203 |
| Vancomycin | | | | | <0.0001 |

The Sig complex in this experiment was found to have a rapid bacteriocidal activity at nanomolar concentrations against MRSA both in vitro and in vivo.

EXAMPLE 7

Delivery of TFDS Mediated by Antibacterial Peptides

Materials and Methods

The following antibacterial peptides were assayed for their ability to deliver TFDs to bacterial cells: Gramicidin, Polymyxin nonapeptide (both purchased from Sigma Aldrich) and Buforin II (Park et al. (2000) *Proc. Natl. Acad. Sci. USA* 97: 8245-8250). Typically 1 µg of the Sig DB-TFDs and SigScr DB-TFD as described in Example 1 were mixed with between 0.2 and 5 µg of Gramicidin in a total volume of 5 µl 50 mM NaCl. Of this, 1 µl was added to 200 µl of LB broth inoculated with a 1/100 dilution of a glycerol stock of EMRSA-15 at an original density of 0.3 OD (Absorbance at 600 nm) and aliquoted into a well of a 96 well plate. Experiments were performed in triplicate. The plates were incubated at 37° C. with shaking and absorbance readings (at 450 nM) were taken using a plate reader.

Results 7.1. Gramicidin Effectively Delivers TFDS to *S. aureus*

Adding 1 µg of Sig DB-TFD to LB media inoculated with EMRSA-15 and with 150 ng/ul of Gramicidin resulted in no bacterial growth. In contrast the TFD alone, Gramicidin alone or Gramicidin mixed with the scrambled version of the DB-TFD grew as well as the untreated control (FIG. 17).

7.2. Buforin II Effectively Delivers TFDs to *S. aureus*

The 21 amino acid Buforin II peptide consisted of the following sequence: TRSSRAGLQFPVGRVHRLLRK (SEQ ID NO:51). Sig TFDs mixed with Buforin II retarded growth of EMRSA-15 when mixed with the membrane-active antimicrobial peptide Buforin II and prevented growth of the bacteria in a 96 well plate in vitro assay. The control TFD, Scr, which was a scrambled version of the sequence in the Sig TFD, had no discernable effect on growth when compared to the untreated broth or the cells treated with peptide alone (FIG. 18).

As an alternative, a fluorescently-labelled oligonucleotide was used as a substitute for the TFD. Though this has no predicted activity as a TFD molecule, the fluorescein-labelled oligonucleotide incorporates a fluorescent label so its uptake can be monitored by fluorescent light microscopy (FIG. 19).

7.3. Polymyxin Effectively Delivers TFDs to *E. coli*

When mixed with the Gram-negative active antimicrobial cyclic glycopeptide polymyxin, EC Fur TFD retarded growth of DH5a and prevented growth of the bacteria in a 96 well plate in vitro assay using iron-limiting media. The control TFD, WhiB7 TFD which was an unrelated sequence of similar size as the Fur TFD, had no discernable effect on growth when compared to the untreated broth or the cells treated with peptide alone (FIG. 20).

EXAMPLE 8

Delivery of TFD/Dequalinium Complexes Conjugated with Buforin II

Materials and Methods

Derivatisation of Complexes with Antimicrobial Peptide

TFD complexes were derivatised with the antimicrobial peptide Buforin II using the cross-linker EDC (1-ethyl-3-[3-dimethylaminopropyl]carbodiimide hydrochloride; Thermo Scientific) and following an adaptation of the two-step coupling protocol as described by the manufacturer.

The Buforin II peptide was synthesised and lyophilised and re-suspended at a concentration of 1 mg/ml in Activation Buffer (0.1 M MES [2-(N-morpholino)ethane sulfonic acid], 0.5 M NaCl, pH6.0). 1 ml of this solution was mixed with 0.4 mg EDC and 1.1 mg Sulfo-NHS (Thermo Scientific) and incubated for between 5 and 120 min at room temperature, most typically 30 min. After incubation, 1.4 µl 2-mercaptoethanol was added to quench the EDC. Unincorporated EDC and Sulfo-NHS were removed from the peptide sample by dialysis using tubing with a low molecular weight cut-off (Pierce, Slide-A-Lyzer, 2K MWCO).

Concentrated TFD complexes were prepared using techniques described in Examples 2 and 3. 35 µl of TFD at a concentration of 1.5 mg/ml was mixed with 130 µl PBS (Phosphate-buffered saline; 0.1 M sodium phosphate buffer pH7.2, 0.15 M NaCl) and 35 µl of sonicated Compound 7 (bolasomes) at a concentration of 3.15 mg/ml. Typically 90 µl of concentrated TFD complexes were mixed with 10 µl of derivatised Buforin II and allowed to react for 2 hours at room temperature. The reaction was quenched by addition of 10 mM hydroxylamine. Prior to use in bioassays the derivatised TFD nanoparticle were diluted to the appropriate concentration.

As an alternative, a fluorescein-labelled oligonucleotide was used as a substitute for the TFD. Though this has no predicted activity as a TFD molecule, the fluorescein-labelled oligonucleotide incorporates a fluorescent label so its uptake can be monitored by fluorescent light microscopy.

Results 8.1. Buforin II-Derivatised TFD Complexes Effectively Deliver Oligonucleotides to *S. aureus*

Derivatised TFD complexes were formed as described, with the exception that the TFD was substituted with a fluorescently labelled oligonucleotide, Tef, that contained a fluorescein dye at the 5' end. The sequence of the oligonucleotide was:

```
                                         SEQ ID NO: 52
Tef-Fluorescein-AGG CGG CCG CGA ATT CAC TAG TGA.
```

The derivatised complexes are added to 200 μl of LB broth inoculated with the MRSA strain, EMRSA-15, and grown overnight with shaking at 37° C. The following morning, cells were harvested by centrifugation and washed four times in an equal volume of PBS. A drop of the bacterial suspension was placed on a microscope slide and air dried. Cells were then heat-fixed by passing the slide through a Bunsen flame. The slide was then flooded with a solution of Loeffler's methylene blue (5 mg/ml methylene blue in 69:30:1 (v/v) solution of water:methanol: 1% (w/v) KOH) and allowed to stand for 1 min, after which the excess solution was washed off with water and the cells visualised using a Cairn CCD Fluorescence Microscope.

In the bright-field view (no fluorescence) the bacteria could be clearly seen clumped together (FIG. 21) and in the fluorescence view it could be seen that the labelled oligonucleotide had been internalised, consistent with the derivatised nanoparticle affecting delivery. Bacteria grown in broth without derivatised complexes showed no fluorescence.

8.2. Buforin II-Derivatised TFD Complexes can Prevent Bacterial Growth of MRSA

Derivatised complexes were produced that contained either the Sig TFD or Scr TFD as a control (as in Example 2). The concentration of the TFD component in the stock of derivatised complexes was 8 μM and the complexes were diluted to give a working concentration of 16 nM TFD and 1.8 μM Compound 7.

At this concentration the derivatised complexes containing the Sig TFD entirely prevented growth of the MRSA strain, while the derivatised complex containing the control TFD did not. Indeed, growth was similar to the untreated sample and the sC7 control broth containing 1.8 μM Compound 7 bolasomes (FIG. 22).

Hence, complexes derivatised with Buforin II deliver Sig TFDs to pathogenic bacteria to prevent growth. Furthermore, the effective concentration of the complexes used was lower than that for the non-derivatised complexes (section 4.1).

EXAMPLE 9

Formation of Complexes with Other Dequalinium Analogues

By following the general synthetic methods described herein, the following dequalinium analogues were prepared:

10,10'-(octane-1,8-diyl)bis(9-amino-1,2,3,4-tetrahydroacridinium)diiodide;

10,10'-(dodecane-1,12-diyl)bis(9-amino-1,2,3,4-tetrahydroacridinium)diiodide;

10,10'-(tetradecane-1,14-diyl)bis(9-amino-1,2,3,4-tetrahydroacridinium)diiodide;

10,10'-(octadecane-1,18-diyl)bis(9-amino-1,2,3,4-tetrahydroacridinium)diiodide;

5,5'-(dodecane-1,12-diyl)bis(11-amino-7,8,9,10-tetrahydro-6H-cyclohepta[b]quinolinium)diiodide;

1,1'-(decane-1,10-diyl)bis(4-aminoquinolinium)diiodide;

1,1'-(dodecane-1,12-diyl)bis(4-aminoquinolinium)diiodide;

1,1'-(decane-1,10-diyl)bis(4-methoxyquinolinium)diiodide; and 1,1'-(decane-1,10-diyl)bis(2-aminoquinolinium)diiodide.

The compounds listed above may be used in the methods described in Examples 1 to 8 to prepare further complexes according to the invention

The invention claimed is:

1. An antibacterial complex comprising a double stranded nucleic acid sequence and at least one delivery moiety, wherein:
   a) the nucleic acid sequence comprises the sequence of a native cellular binding site for a bacterial transcription factor and is 40 to 100 nucleotides in length and self-anneals to form the binding site for the bacterial transcription factor; and
   b) the delivery moiety has the formula:

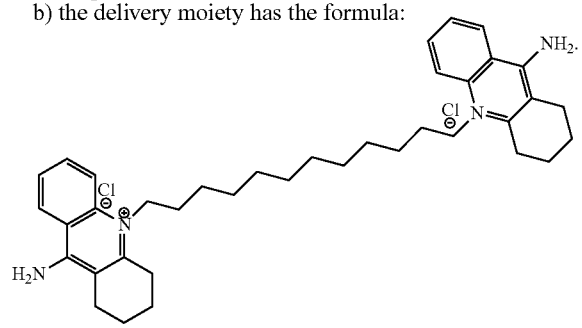

2. The complex according to claim 1, wherein the native cellular binding site comprises the sequence of a bacterial SigB binding site and optionally the nucleic acid sequence has the sequence set out in SEQ ID NOs:9, 10, 30 and 31, 39, 40 or 41.

3. The complex according to claim 1, wherein the native cellular binding site comprises the sequence of a bacterial Fur binding site or the nucleic acid sequence has the sequence set out in SEQ ID NOs:11, 12 or 13.

* * * * *

SEQUENCE LISTING

```
<160> NUMBER OF SEQ ID NOS: 52

<210> SEQ ID NO 1
<211> LENGTH: 106
<212> TYPE: DNA
<213> ORGANISM: Mycobacterium smegmatis

<400> SEQUENCE: 1
caccagccga aaaggccacg gacccgcagt cacccggatc cgtggccatt tttgtcggac      60
cccccgagaa atctggtcgc aggatccatc agctcagaca gatcac                   106
```

<210> SEQ ID NO 2
<211> LENGTH: 36
<212> TYPE: DNA
<213> ORGANISM: Mycobacterium smegmatis

<400> SEQUENCE: 2
tggccacgga tccgggtgac tgcgggtccg tggcct                              36

<210> SEQ ID NO 3
<211> LENGTH: 63
<212> TYPE: DNA
<213> ORGANISM: Escherichia coli

<400> SEQUENCE: 3
agtaagtttc gaatgcacaa tagcgtacac ttgtacgccg aacaagtccg atcagccatt   60
taa                                                                 63

<210> SEQ ID NO 4
<211> LENGTH: 60
<212> TYPE: DNA
<213> ORGANISM: Escherichia coli

<400> SEQUENCE: 4
tttattccga actgatcgga cttgttcagc gtacacgtgt tagctatcct gcgtgcttca   60

<210> SEQ ID NO 5
<211> LENGTH: 38
<212> TYPE: DNA
<213> ORGANISM: Staphylococcus aureus

<400> SEQUENCE: 5
gctattttgt aatgacaatg taatgagttt agtaaaaa                            38

<210> SEQ ID NO 6
<211> LENGTH: 28
<212> TYPE: DNA
<213> ORGANISM: Staphylococcus aureus

<400> SEQUENCE: 6
attacaaatt tgtaacagac ttattta                                        28

<210> SEQ ID NO 7
<211> LENGTH: 38
<212> TYPE: DNA
<213> ORGANISM: Staphylococcus aureus

<400> SEQUENCE: 7
gctattttgt aatgacaatg taatgagttt agtaaaaa                            38

<210> SEQ ID NO 8
<211> LENGTH: 28
<212> TYPE: DNA
<213> ORGANISM: Staphylococcus aureus

<400> SEQUENCE: 8
attacaaatt tgtaacagac ttattta                                        28

<210> SEQ ID NO 9
<211> LENGTH: 35
<212> TYPE: DNA
<213> ORGANISM: Staphylococcus aureus

<400> SEQUENCE: 9

```
ttattatata cccatcgaaa taatttctaa tcttc                               35

<210> SEQ ID NO 10
<211> LENGTH: 30
<212> TYPE: DNA
<213> ORGANISM: Klebsiella pneumoniae

<400> SEQUENCE: 10
ccgataaggg cgcacggttt gcatggttat                                     30

<210> SEQ ID NO 11
<211> LENGTH: 32
<212> TYPE: DNA
<213> ORGANISM: Staphylococcus aureus

<400> SEQUENCE: 11
actacaagta ctattagtaa tagttaaccc tt                                  32

<210> SEQ ID NO 12
<211> LENGTH: 19
<212> TYPE: DNA
<213> ORGANISM: Escherichia coli

<400> SEQUENCE: 12
gataatgata atcattatc                                                 19

<210> SEQ ID NO 13
<211> LENGTH: 42
<212> TYPE: DNA
<213> ORGANISM: Helicobacter pylori

<400> SEQUENCE: 13
gttgtcccat aattatagca taaatgataa tgaaaagta aa                        42

<210> SEQ ID NO 14
<211> LENGTH: 36
<212> TYPE: DNA
<213> ORGANISM: Clostridium difficile

<400> SEQUENCE: 14
aagtttacaa aattatatta gaataacttt tttatt                              36

<210> SEQ ID NO 15
<211> LENGTH: 22
<212> TYPE: DNA
<213> ORGANISM: Pseudomonas aeruginosa

<400> SEQUENCE: 15
aaatgtgatc tagatcacat tt                                             22

<210> SEQ ID NO 16
<211> LENGTH: 26
<212> TYPE: DNA
<213> ORGANISM: Pseudomonas aeruginosa

<400> SEQUENCE: 16
cactctgcaa tccagttcat aaatcc                                         26

<210> SEQ ID NO 17
<211> LENGTH: 23
<212> TYPE: DNA
<213> ORGANISM: Pseudomonas aeruginosa
```

```
<400> SEQUENCE: 17
gtaacagcgg aaccactgca cag                                              23

<210> SEQ ID NO 18
<211> LENGTH: 43
<212> TYPE: DNA
<213> ORGANISM: Klebsiella pneumoniae

<400> SEQUENCE: 18
gctttgcact accgcggccc atccctgccc caaaacgatc gct                        43

<210> SEQ ID NO 19
<211> LENGTH: 56
<212> TYPE: DNA
<213> ORGANISM: Helicobacter pylori

<400> SEQUENCE: 19
ataatcataa tgattaaagt tttcatattc attataaatc cgtttacaca attatt          56

<210> SEQ ID NO 20
<211> LENGTH: 61
<212> TYPE: DNA
<213> ORGANISM: Helicobacter pylori

<400> SEQUENCE: 20
gaaattgttc tatttattat ccatttgctt attaataatt ggttgttaat tttggtttag      60
a                                                                     61

<210> SEQ ID NO 21
<211> LENGTH: 17
<212> TYPE: DNA
<213> ORGANISM: Staphylococcus aureus

<400> SEQUENCE: 21
tgaacacctt cttttta                                                    17

<210> SEQ ID NO 22
<211> LENGTH: 20
<212> TYPE: DNA
<213> ORGANISM: Staphylococcus aureus

<400> SEQUENCE: 22
agaaagacaa acaggagtaa                                                 20

<210> SEQ ID NO 23
<211> LENGTH: 20
<212> TYPE: DNA
<213> ORGANISM: Staphylococcus aureus

<400> SEQUENCE: 23
gaagaaacaa aaagcagcat                                                 20

<210> SEQ ID NO 24
<211> LENGTH: 35
<212> TYPE: DNA
<213> ORGANISM: Staphylococcus aureus

<400> SEQUENCE: 24
gaagattaga aattatttcg atgggtatat aataa                                35

<210> SEQ ID NO 25
<211> LENGTH: 35
```

<212> TYPE: DNA
<213> ORGANISM: Staphylococcus aureus

<400> SEQUENCE: 25
tattatatac ccatcgaaat aatttctaat cttca                          35

<210> SEQ ID NO 26
<211> LENGTH: 32
<212> TYPE: DNA
<213> ORGANISM: Staphylococcus aureus

<400> SEQUENCE: 26
actacaagta ctattagtaa tagttaaccc ta                             32

<210> SEQ ID NO 27
<211> LENGTH: 32
<212> TYPE: DNA
<213> ORGANISM: Staphylococcus aureus

<400> SEQUENCE: 27
agggttaact attactaata gtacttgtag ta                             32

<210> SEQ ID NO 28
<211> LENGTH: 28
<212> TYPE: DNA
<213> ORGANISM: Staphylococcus aureus

<400> SEQUENCE: 28
attacaaatt tgtaacagac ttatttta                                  28

<210> SEQ ID NO 29
<211> LENGTH: 28
<212> TYPE: DNA
<213> ORGANISM: Staphylococcus aureus

<400> SEQUENCE: 29
aaaataagtc tgttacaaat ttgtaata                                  28

<210> SEQ ID NO 30
<211> LENGTH: 49
<212> TYPE: DNA
<213> ORGANISM: Artificial Sequence
<220> FEATURE:
<223> OTHER INFORMATION: Phosphorylated Sig dumbbell TFD sequence
      synthesized and derived from S. aureus

<400> SEQUENCE: 30
cttggttttt ccaaggaaga ttagaaatta tttcgatggg tatataata            49

<210> SEQ ID NO 31
<211> LENGTH: 49
<212> TYPE: DNA
<213> ORGANISM: Artificial Sequence
<220> FEATURE:
<223> OTHER INFORMATION: Phosphorylated Sig dumbbell TFD sequence
      synthesized and derived from S. aureus

<400> SEQUENCE: 31
ccgtcttttt gacggtatta tatacccatc gaaataattt ctaatcttc            49

<210> SEQ ID NO 32
<211> LENGTH: 57
<212> TYPE: DNA
<213> ORGANISM: Staphylococcus aureus

<400> SEQUENCE: 32
cttggttttt ccaagtaatg aatgagttta aagcccatgt aaaagggta tcagtac        57

<210> SEQ ID NO 33
<211> LENGTH: 57
<212> TYPE: DNA
<213> ORGANISM: Staphylococcus aureus

<400> SEQUENCE: 33
ccctcttttt gagggtact gatacccctt ttacatgggc tttaaactca ttcatta        57

<210> SEQ ID NO 34
<211> LENGTH: 24
<212> TYPE: DNA
<213> ORGANISM: Staphylococcus aureus

<400> SEQUENCE: 34
tctttaaatg gctgatcgga cttg                                            24

<210> SEQ ID NO 35
<211> LENGTH: 27
<212> TYPE: DNA
<213> ORGANISM: Staphylococcus aureus

<400> SEQUENCE: 35
agtaagtttc gaatgcacaa tagcgta                                         27

<210> SEQ ID NO 36
<211> LENGTH: 31
<212> TYPE: DNA
<213> ORGANISM: Klebsiella pneumoniae

<400> SEQUENCE: 36
ccgataaggg cgcacggttt gcatggttat a                                    31

<210> SEQ ID NO 37
<211> LENGTH: 31
<212> TYPE: DNA
<213> ORGANISM: Klebsiella pneumoniae

<400> SEQUENCE: 37
ataaccatgc aaaccgtgcg cccttatcgg a                                    31

<210> SEQ ID NO 38
<211> LENGTH: 17
<212> TYPE: DNA
<213> ORGANISM: Artificial Sequence
<220> FEATURE:
<223> OTHER INFORMATION: WalR TFD consensus sequence synthesized and
      derived from S. aureus
<220> FEATURE:
<221> NAME/KEY: misc_feature
<222> LOCATION: (7)..(11)
<223> OTHER INFORMATION: n is a, c, g, or t

<400> SEQUENCE: 38
tgtwawnnnn ntgtaaw                                                    17

<210> SEQ ID NO 39
<211> LENGTH: 26
<212> TYPE: DNA
<213> ORGANISM: Artificial Sequence
<220> FEATURE:
<223> OTHER INFORMATION: SigB TFD consensus sequence synthesized and
      derived from S. aureus

```
<220> FEATURE:
<221> NAME/KEY: misc_feature
<222> LOCATION: (7)..(20)
<223> OTHER INFORMATION: n is a, c, g, or t

<400> SEQUENCE: 39
gkttwannnn nnnnnnnnnn kggtaw                                          26

<210> SEQ ID NO 40
<211> LENGTH: 16
<212> TYPE: DNA
<213> ORGANISM: Klebsiella pneumoniae

<400> SEQUENCE: 40
tggcacagat ttcgct                                                     16

<210> SEQ ID NO 41
<211> LENGTH: 16
<212> TYPE: DNA
<213> ORGANISM: Artificial Sequence
<220> FEATURE:
<223> OTHER INFORMATION: KP-Sig TFD sequence derived from Klebsiella
      pneumoniae
<220> FEATURE:
<221> NAME/KEY: misc_feature
<222> LOCATION: (4)..(9)
<223> OTHER INFORMATION: n is a, c, g, or t

<400> SEQUENCE: 41
tggnnnnnnw tttgcw                                                     16

<210> SEQ ID NO 42
<211> LENGTH: 40
<212> TYPE: DNA
<213> ORGANISM: Artificial Sequence
<220> FEATURE:
<223> OTHER INFORMATION: Gram negative Sig TFD hairpin sequence
      synthesized and derived from E. coli, P. aeruginosa and K.
      pneumoniae

<400> SEQUENCE: 42
gcgaagcgtg ataatcatta tcggagataa tgattatcac                           40

<210> SEQ ID NO 43
<211> LENGTH: 49
<212> TYPE: DNA
<213> ORGANISM: Artificial Sequence
<220> FEATURE:
<223> OTHER INFORMATION: Primer for scrambled S. aureus Sig binding
      site, derived from S. aureus

<400> SEQUENCE: 43
cttggttttt ccaagtagaa agaagattta gggcgatttt ataatatat                 49

<210> SEQ ID NO 44
<211> LENGTH: 49
<212> TYPE: DNA
<213> ORGANISM: Artificial Sequence
<220> FEATURE:
<223> OTHER INFORMATION: Primer for scrambled S. aureus Sig binding
      site, derived from S. aureus

<400> SEQUENCE: 44
ccgtcttttt gacggatata ttataaaatc gccctaaatc ttctttcta                 49

<210> SEQ ID NO 45
<211> LENGTH: 26
```

-continued

<212> TYPE: DNA
<213> ORGANISM: Artificial Sequence
<220> FEATURE:
<223> OTHER INFORMATION: Primer used for amplification of a target
      sequence from the pGEMT-Easy vector

<400> SEQUENCE: 45
ggccgccatg gcggccgcgg gaattc                                          26

<210> SEQ ID NO 46
<211> LENGTH: 23
<212> TYPE: DNA
<213> ORGANISM: Artificial Sequence
<220> FEATURE:
<223> OTHER INFORMATION: Primer used for amplification of a target
      sequence from the pGEMT-Easy vector

<400> SEQUENCE: 46
aggcggccgc gaattcacta gtg                                             23

<210> SEQ ID NO 47
<211> LENGTH: 21
<212> TYPE: DNA
<213> ORGANISM: Mycobacterium smegmatis

<400> SEQUENCE: 47
caccagccga aaaggccacg g                                               21

<210> SEQ ID NO 48
<211> LENGTH: 24
<212> TYPE: DNA
<213> ORGANISM: Mycobacterium smegmatis

<400> SEQUENCE: 48
caaaaatggc cacggatccg ggtg                                            24

<210> SEQ ID NO 49
<211> LENGTH: 90
<212> TYPE: DNA
<213> ORGANISM: Staphylococcus aureus

<400> SEQUENCE: 49
gcgaagcgaa gattagaaat tatttccatg ggtatataat acttggtttt tccaagtatt     60
atatacccat ggaaataatt tctaatcttc                                      90

<210> SEQ ID NO 50
<211> LENGTH: 90
<212> TYPE: DNA
<213> ORGANISM: Artificial Sequence
<220> FEATURE:
<223> OTHER INFORMATION: SA_Sig scrambled hairpin TFD sequence
      synthesized and derived from S. aureus

<400> SEQUENCE: 50
gcgaagcatc ttgtatgcaa atagaatgaa taatagtttg acttggtttt tccaagtcaa     60
actattattc attctatttg catacaagat                                      90

<210> SEQ ID NO 51
<211> LENGTH: 21
<212> TYPE: PRT
<213> ORGANISM: Artificial Sequence
<220> FEATURE:
<223> OTHER INFORMATION: Buforin II peptide sequence synthesized in lab

<400> SEQUENCE: 51

```
Thr Arg Ser Ser Arg Ala Gly Leu Gln Phe Pro Val Gly Arg Val His
1               5                   10                  15

Arg Leu Leu Arg Lys
            20

<210> SEQ ID NO 52
<211> LENGTH: 24
<212> TYPE: DNA
<213> ORGANISM: Staphylococcus aureus

<400> SEQUENCE: 52
aggcggccgc gaattcacta gtga                                          24
```